US011083850B2

(12) United States Patent
Hatamian et al.

(10) Patent No.: US 11,083,850 B2
(45) Date of Patent: *Aug. 10, 2021

(54) SECURE SMART DOSING SYSTEM WITH AUTOMATED DELIVERY, MEASUREMENT, AND MANAGEMENT

(71) Applicant: Vivera Pharmaceuticals Inc., Las Vegas, NV (US)

(72) Inventors: Mehdi Hatamian, Mission Viejo, CA (US); Paul Edalat, Newport Beach, CA (US)

(73) Assignee: Vivera Pharmaceuticals Inc., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/570,546

(22) Filed: Sep. 13, 2019

(65) Prior Publication Data

US 2020/0061301 A1    Feb. 27, 2020

Related U.S. Application Data

(63) Continuation-in-part of application No. 16/106,575, filed on Aug. 21, 2018.

(51) Int. Cl.
*G16H 20/13* (2018.01)
*A61M 11/04* (2006.01)
(Continued)

(52) U.S. Cl.
CPC .... *A61M 5/31541* (2013.01); *A61M 5/31546* (2013.01); *A61M 5/31568* (2013.01);
(Continued)

(58) Field of Classification Search
CPC .............. A61M 15/00; A61M 15/0001; A61M 15/0003; A61M 15/0011; A61M 15/0021;
(Continued)

(56) References Cited

U.S. PATENT DOCUMENTS

| 5,038,769 A | 8/1991 | Krauser |
| 6,737,042 B2 | 5/2004 | Rabinowitz et al. |

(Continued)

FOREIGN PATENT DOCUMENTS

| WO | 2002094234 A1 | 11/2002 |
| WO | 2013028705 A2 | 2/2013 |

(Continued)

OTHER PUBLICATIONS

Marc Cohen, Wireless Monitoring/Reward System for Asthma Inhaler Use Mar. 2007, , , National Institutes of Health, Evanston IL.

(Continued)

*Primary Examiner* — Tu A Vo
(74) *Attorney, Agent, or Firm* — Genius Patent APC; Brace Angus Hare

(57) ABSTRACT

A smart dosing device includes: a flow pathway having a cartridge receptacle that is able to house a cartridge; at least one sensor that captures identifying information related to the cartridge; a wireless communication module; and at least one security feature that restricts use of the smart dosing device. A method of providing a measured dose using a smart dosing device includes: enabling dosing; measuring a provided dose; and disabling dosing. A smart dosing system includes: a smart dosing device having a unique identifier, the smart dosing device including a cartridge housing a substance, the cartridge having a unique cartridge identifier; and a server including a central database that stores usage information related to the smart dosing device, the usage information including: the unique identifier and the unique cartridge identifier.

15 Claims, 20 Drawing Sheets

(51) Int. Cl.

| | | |
|---|---|---|
| *A61M 5/315* | (2006.01) | |
| *A61M 15/00* | (2006.01) | |
| *A61M 5/00* | (2006.01) | |
| *A61M 11/00* | (2006.01) | |
| *A61M 15/06* | (2006.01) | |
| *A61M 5/31* | (2006.01) | |
| *A61K 31/465* | (2006.01) | |
| *A61K 31/352* | (2006.01) | |
| *H04W 12/084* | (2021.01) | |
| *G16H 40/63* | (2018.01) | |

(52) U.S. Cl.
CPC .......... *A61M 11/042* (2014.02); *G16H 20/13* (2018.01); *A61K 31/352* (2013.01); *A61K 31/465* (2013.01); *A61M 5/31571* (2013.01); *A61M 15/002* (2014.02); *A61M 15/0003* (2014.02); *A61M 15/0021* (2014.02); *A61M 15/0066* (2014.02); *A61M 15/0083* (2014.02); *A61M 2005/3126* (2013.01); *A61M 2205/3303* (2013.01); *A61M 2205/3306* (2013.01); *A61M 2205/3331* (2013.01); *A61M 2205/3334* (2013.01); *A61M 2205/3368* (2013.01); *A61M 2205/3375* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/505* (2013.01); *A61M 2205/60* (2013.01); *A61M 2205/609* (2013.01); *A61M 2205/6063* (2013.01); *A61M 2205/6072* (2013.01); *A61M 2205/8206* (2013.01); *G16H 40/63* (2018.01); *H04W 12/084* (2021.01)

(58) Field of Classification Search
CPC .......... A61M 16/201; A61M 15/0065; A61M 15/0068; A61M 15/0071; A61M 15/009; A61M 15/0091; A61M 15/06; A61M 15/08; A61M 11/00; A61M 11/02; A61M 11/04; A61M 11/06; A61M 11/08; A61M 2205/502; A61M 2202/04; A61M 5/31541; A61M 5/31546; A61M 5/31568; A61M 5/31571; G16H 20/13; H04W 12/084

See application file for complete search history.

(56) References Cited

U.S. PATENT DOCUMENTS

| | | | |
|---|---|---|---|
| 8,550,069 B2 | 10/2013 | Alelov | |
| 2004/0172162 A1* | 9/2004 | Bonney | A61M 15/00 700/237 |
| 2007/0186923 A1* | 8/2007 | Poutiatine | A61J 7/0038 128/200.14 |
| 2007/0240712 A1* | 10/2007 | Fleming | A61M 15/0028 128/203.15 |
| 2008/0011292 A1* | 1/2008 | Sugita | A61M 5/16827 128/200.19 |
| 2008/0164275 A1 | 7/2008 | Poutiatine et al. | |
| 2010/0105735 A1* | 4/2010 | Palmer | A61J 7/0038 514/326 |
| 2010/0305750 A1 | 12/2010 | Conley | |
| 2012/0035760 A1* | 2/2012 | Portney | G16H 20/13 700/231 |
| 2012/0174914 A1* | 7/2012 | Pirshafiey | A61M 11/041 128/200.14 |
| 2013/0197693 A1* | 8/2013 | Kamen | G16H 20/17 700/244 |
| 2013/0220315 A1* | 8/2013 | Conley | H05B 1/0244 128/202.21 |
| 2013/0261794 A1* | 10/2013 | Fauci | A61J 7/0076 700/237 |
| 2013/0269694 A1 | 10/2013 | Patton et al. | |
| 2013/0284192 A1 | 10/2013 | Peleg et al. | |
| 2014/0246035 A1* | 9/2014 | Minskoff | A24F 47/008 131/329 |
| 2014/0322682 A1* | 10/2014 | Baym | G09B 5/02 434/219 |
| 2015/0112707 A1* | 4/2015 | Manice | A61M 15/008 705/2 |
| 2015/0122252 A1* | 5/2015 | Frija | A24F 47/008 128/202.21 |
| 2015/0136158 A1* | 5/2015 | Stevens | A24F 47/008 131/329 |
| 2015/0272220 A1 | 10/2015 | Spinka et al. | |
| 2016/0089508 A1* | 3/2016 | Smith | A61M 15/06 128/200.16 |
| 2016/0157524 A1* | 6/2016 | Bowen | G01N 33/0027 128/200.14 |
| 2016/0309789 A1* | 10/2016 | Thomas, Jr. | A24F 47/008 |
| 2016/0325055 A1* | 11/2016 | Cameron | A61M 11/005 |
| 2016/0325057 A1 | 11/2016 | Morrison et al. | |
| 2016/0330999 A1* | 11/2016 | Cameron | B01B 1/005 |
| 2016/0331023 A1* | 11/2016 | Cameron | A24F 47/002 |
| 2016/0331026 A1* | 11/2016 | Cameron | A24F 47/002 |
| 2016/0331027 A1* | 11/2016 | Cameron | A24F 47/002 |
| 2016/0331034 A1* | 11/2016 | Cameron | A24F 47/008 |
| 2016/0331035 A1 | 11/2016 | Cameron | |
| 2016/0331036 A1* | 11/2016 | Cameron | H04M 1/7253 |
| 2016/0337362 A1* | 11/2016 | Cameron | H04L 63/10 |
| 2016/0363570 A1* | 12/2016 | Blackley | G01N 33/0006 |
| 2016/0366946 A1* | 12/2016 | Murison | A24F 15/12 |
| 2017/0014582 A1* | 1/2017 | Skoda | A61M 11/042 |
| 2017/0055588 A1* | 3/2017 | Cameron | H05B 3/44 |
| 2017/0095624 A1 | 4/2017 | Davidson et al. | |
| 2017/0099877 A1* | 4/2017 | Worm | A61M 11/042 |
| 2017/0106153 A1 | 4/2017 | Davidson et al. | |
| 2017/0136193 A1* | 5/2017 | Cameron | A61M 11/042 |
| 2017/0136194 A1* | 5/2017 | Cameron | A61M 11/042 |
| 2017/0136196 A1 | 5/2017 | Davidson et al. | |
| 2017/0157343 A1 | 6/2017 | Davidson et al. | |
| 2017/0181474 A1* | 6/2017 | Cameron | A24F 47/008 |
| 2017/0181475 A1* | 6/2017 | Cameron | A24F 47/008 |
| 2017/0182267 A1* | 6/2017 | Cameron | A61M 11/042 |
| 2017/0304563 A1* | 10/2017 | Adelson | A61M 15/06 |
| 2017/0368273 A1* | 12/2017 | Rubin | A61M 11/042 |
| 2018/0020727 A1* | 1/2018 | Hoffman | H02J 7/00 131/328 |
| 2018/0110939 A1* | 4/2018 | Lanzkowsky | A61K 9/007 |
| 2018/0256835 A1* | 9/2018 | Fornarelli | A61M 15/0083 |
| 2018/0289907 A1* | 10/2018 | Marmur | A61M 11/001 |
| 2018/0295886 A1* | 10/2018 | Freeman | A24F 47/008 |
| 2018/0369516 A1* | 12/2018 | Adelson | A61M 15/0025 |
| 2019/0134324 A1* | 5/2019 | Rabinowitz | A61M 15/06 |
| 2019/0158938 A1 | 5/2019 | Bowen et al. | |
| 2019/0167927 A1 | 6/2019 | Dagnello et al. | |
| 2019/0240430 A1* | 8/2019 | Jackson | A61M 15/008 |
| 2020/0061314 A1 | 2/2020 | Hatamian et al. | |

FOREIGN PATENT DOCUMENTS

| | | |
|---|---|---|
| WO | 2014145218 A2 | 9/2014 |
| WO | 2015148547 A1 | 1/2015 |
| WO | 20160333419 A1 | 3/2016 |
| WO | 2016090303 A1 | 6/2016 |
| WO | 2016092259 A1 | 6/2016 |
| WO | 2016187110 A1 | 11/2016 |
| WO | 2016187111 A1 | 11/2016 |
| WO | 2017005605 A1 | 1/2017 |
| WO | 2018064377 A1 | 4/2018 |
| WO | 2020041430 A1 | 2/2020 |

OTHER PUBLICATIONS

Mike Marett et al., Fully-Connected Metered Dose Inhaler to Optimize Care of Asthma and COPD, CISION PRWeb, Dec. 2016, , , PRWeb, Edinburgh, Scotland.

(56) References Cited

OTHER PUBLICATIONS

My Health Portal, Wireless inhaler that connects patients to doctors, Employee on-line medical health blog, May 2009.

* cited by examiner

SECURE SMART DOSING SYSTEM WITH AUTOMATED DELIVERY, MEASUREMENT, AND MANAGEMENT

CROSS-REFERENCE TO RELATED APPLICATIONS

This application is a continuation-in-part of U.S. patent application Ser. No. 16/106,575, filed on Aug. 21, 2018.

BACKGROUND

Many substances may be consumed by users. Such substances may include controlled and uncontrolled substances. Such substances may be provided for medical and/or recreational use. The substances may include, for instance, prescription opioids, cannabinoids, nicotine-based solutions, etc.

Current delivery methods rely on a user to control dosage and security of the substances, if needed. In addition, current delivery methods do not monitor (or indicate) consumed amount or other usage data.

Therefore, there is a need for a secure dosing device that is able to monitor consumption and automatically control dosage.

SUMMARY

Some embodiments may provide a smart dosing device. The dosing device may be configurable and/or customizable such that substances in different forms may be provided by the dosing device. For instance, some embodiments, may provide vaporized or atomized liquids. As another example, some embodiments may provide a measured amount of liquid or powder. As still another example some embodiments may provide a number of discrete doses, such as a number of pills.

The dosing device may be an inhaler-type device that is able to dispense various fluid solutions after vaporizing or atomizing such a solution, a dispensing-type device that directly delivers a solution in liquid form, and/or other device type as appropriate for the dispensed substance. Dispensed substances may include, for instance, opioids, cannabinoids, nicotine-based substances, medications, etc.

Some embodiments may include flow meters and/or other measurement elements that are able to quantify an amount of a substance that is dispensed. Such devices may provide a measured dose of a substance. In this way, users may be able to administer doses in consistent amounts that may match prescriptions or other guidelines associated with use.

Alternatively, such devices may measure an amount of each received dose. Such measurements may allow users to track usage and monitor overall consumption.

Some embodiments of the dosing device may include various sensors such as cameras, near field communication (NFC) scanners, etc. that may be used to automatically identify cartridges used by the smart dosing device. In addition, such sensors may include environmental sensors and/or other appropriate sensors that may be relevant to use of the provided substance.

The dosing device may include an output assist blower that may aid in supplying vaporized substances to users that may have medical conditions or other limitations that would otherwise prevent the users from receiving a full dose or accurately measuring a received dose.

Some embodiments may include a security module that may capture data such as a fingerprint scan and/or facial photograph in order to compare the captured data to reference data and determine whether a user is authorized to use the dosing device. Some embodiments may combine security features or otherwise capture usage information for later analysis. For instance, during dosing, a fingerprint scan may enable dosing (and also be captured and stored) while a camera captures a photo of the current device user or usage environment for later verification or analysis.

In some embodiments, the dosing device may include various user interface (UI) elements. Such UI elements may include, for instance, buttons, displays, indicator lights, touchscreens, etc. In addition, the dosing device may be able to utilize inputs received from an external device (e.g., a smartphone) and/or provide received inputs to such an external device.

The dosing device may be able to communicate with various user devices (e.g., smartphones, tablets, personal computers, etc.) across wired or wireless channels that may include one or more networks. Such user devices may execute an application associated with some embodiments that may allow a user to register a device, download usage information, adjust device settings, and/or otherwise interact with the dosing device.

The dosing device and/or user device may upload information to and/or download information from a resource such as a server or remote storage. Such information may include, for instance, usage data, user information, prescription information, usage instructions, etc. In addition, such information may include software updates, operating parameters, and/or other relevant information used by the dosing device or user device.

The collected information may be shared across various platforms with various appropriate users or entities. For instance, a medical practitioner may be able to access usage data associated with a patient. As another example, a clinical study may be supplied with anonymous usage data.

Some embodiments may provide a usage management system that is able to link users or patients, medical practitioners, pharmacists or other dispensers, and/or other appropriate parties (e.g., a parent or guardian, caretaker, insurance provider, etc.). The usage management system may integrate with existing prescription and substance control policies and procedures.

For example, a prescription for a particular patient may be generated by a medical practitioner. The prescription may be downloaded or entered into the device of some embodiments. The patient may fill the prescription at a pharmacy or other dispensary (which may also provide the device itself). Depending on the nature of the prescribed substance, various security protocols may be implemented to tie use of the substance to a particular patient. For instance, the pharmacist may register the dosing device, a cartridge associated with the prescribed substance, and the patient. Usage data may be collected and provided to interested parties such as the prescribing practitioner. Such a system may be integrated with the security module of some embodiments such that usage is limited to the particular patient.

The preceding Summary is intended to serve as a brief introduction to various features of some exemplary embodiments. Other embodiments may be implemented in other specific forms without departing from the scope of the disclosure.

BRIEF DESCRIPTION OF THE SEVERAL VIEWS OF THE DRAWINGS

The novel features of the disclosure are set forth in the appended claims. However, for purpose of explanation, several embodiments are illustrated in the following drawings.

DETAILED DESCRIPTION

The following detailed description describes currently contemplated modes of carrying out exemplary embodiments. The description is not to be taken in a limiting sense, but is made merely for the purpose of illustrating the general principles of some embodiments, as the scope of the disclosure is best defined by the appended claims.

Various features are described below that can each be used independently of one another or in combination with other features. Broadly, some embodiments generally provide a dosing device with automated security, dose delivery, measurement, and management.

Figure 1:
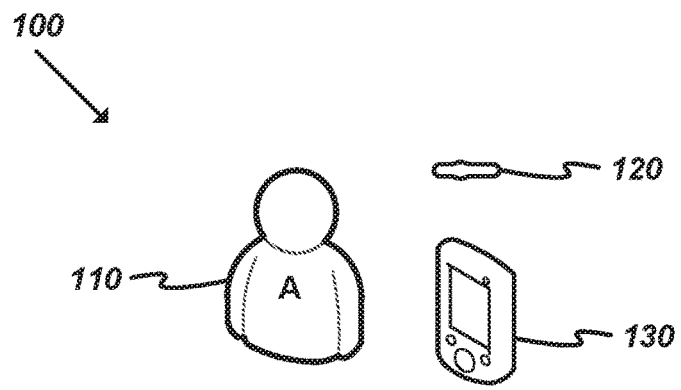
FIG. 1 illustrates a perspective view of a dosing system according to an exemplary embodiment.

FIG. 1 illustrates a perspective view of a dosing system 100 according to an exemplary embodiment. As shown, a user 110 may be associated with a dosing device of some embodiments 120 and a user device 130. Various exemplary dosing devices 120 will be described in more detail in Section I below. The user device 130 may be a smartphone, tablet, personal computer, wearable device, etc. that is able to interact with the dosing device 120 (e.g., via a wired or wireless communication channel).

Throughout this description, many examples will describe a single user 110 associated with a single dosing device 120 and a single user device 130. One of ordinary skill in the art will recognize that various other arrangements may be implemented without departing from the scope of the disclosure. For instance, a single user 110 may be associated with multiple dosing devices 120 and/or multiple user devices 120. Likewise, a single dosing device 120 or user device 130 may be associated with multiple users 110 or multiple other devices 120 or 130.

Figure 2:
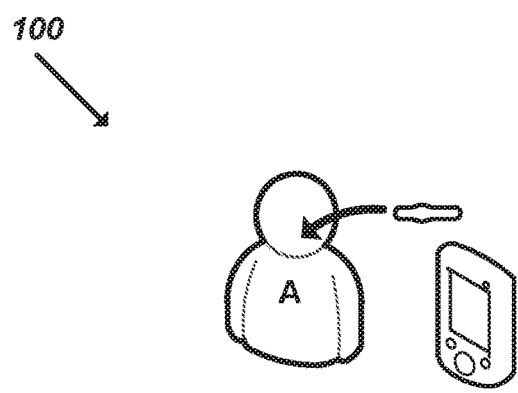
FIG. 2 illustrates a perspective view of the dosing system of FIG. 1 during authorized usage.

FIG. 2 illustrates a perspective view of the dosing system 100 during authorized usage. As shown, an authorized user 110 (user "A") may be able to utilize the device 120 and receive a dose of the associated substance. As will be described in more detail below, the user may also utilize the user device 130 to enable or evaluate dosing.

Figure 3:
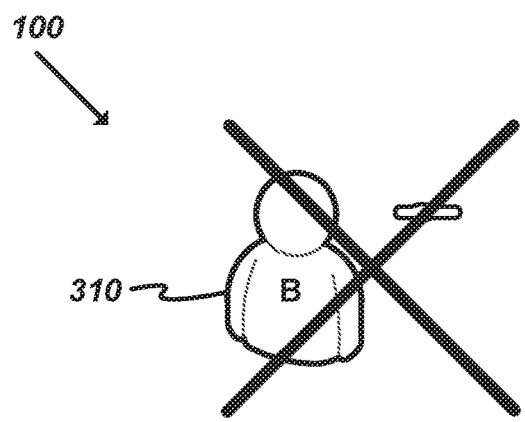
FIG. 3 illustrates a perspective view of the dosing system of FIG. 1 during an unauthorized usage attempt.

FIG. 3 illustrates a perspective view of the dosing system 100 during an unauthorized usage attempt. In this example an unauthorized user 310 (user "B") is not able to utilize the device 120 associated with user A 110. The dosing device 120 may communicate with user device 130 or other resources (e.g., a web server of some embodiments) to generate an alert or other indication of attempted unauthorized use.

Users may be authorized (and/or unauthorized use may be detected) in various appropriate ways. For instance, some dosing devices 120 may include a fingerprint scanner or other biometric evaluation feature that is able to identify an authorized user. As another example, some embodiments may be use passwords, codes, or other similar features to limit device usage. Finally, some embodiments may include mechanical features (e.g., locks, cases, etc.) that may be used to limit access to the dosed substance.

Figure 4:
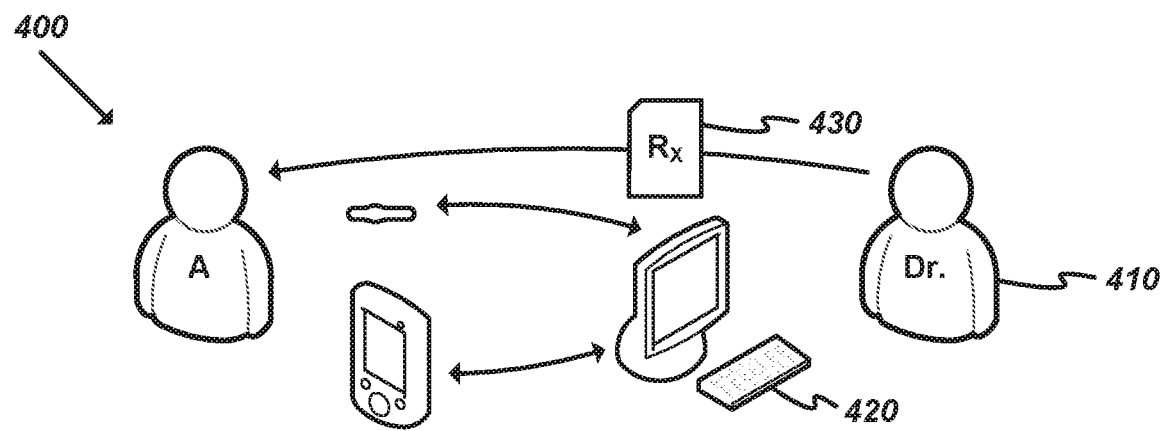
FIG. 4 illustrates a perspective view of the dosing system of FIG. 1 as used during a visit to a medical practitioner.

FIG. 4 illustrates a perspective view of the dosing system 100 as used during a visit to a medical practitioner 410. In this usage scenario 400, a patient 110 (user A). May visit a practitioner 410 that is able to prescribe various controlled substances (i.e., a substance that is regulated by one or more official agencies). The practitioner may be associated with a device 420 (e.g., a mobile device, personal computer, workstation, medical device, etc.) that is able to interact with the dosing device 120 and/or the user device 130. The practitioner device 420 may be associated with a docking station or other resource such that a dosing application or device interface is launched automatically when the dosing device 120 is coupled to the docking station (and/or otherwise coupled to the practitioner device 420).

Each practitioner may be required to register with system of some embodiments. Such registration may include verification of the practitioner's license, status, and/or other appropriate credentials.

Current regulations require a paper prescription 430 to be delivered to the patient 110 and for the patient to physically take the prescription to a pharmacy to be filled. Data associated with the prescription (e.g., dose amounts, schedule, usage limits, warnings, etc.) may be uploaded to either or both devices 120-130. As regulations may evolve, system 100 has the capability to allow prescription information to be delivered directly to the dosing device 120 and/or the user device 130 (or to another appropriate resource such as a server of some embodiments). In addition, the practitioner 410 may download data from either or both devices 120-130 (e.g., usage history including amounts and schedule, unauthorized usage attempts, etc.).

Figure 5:
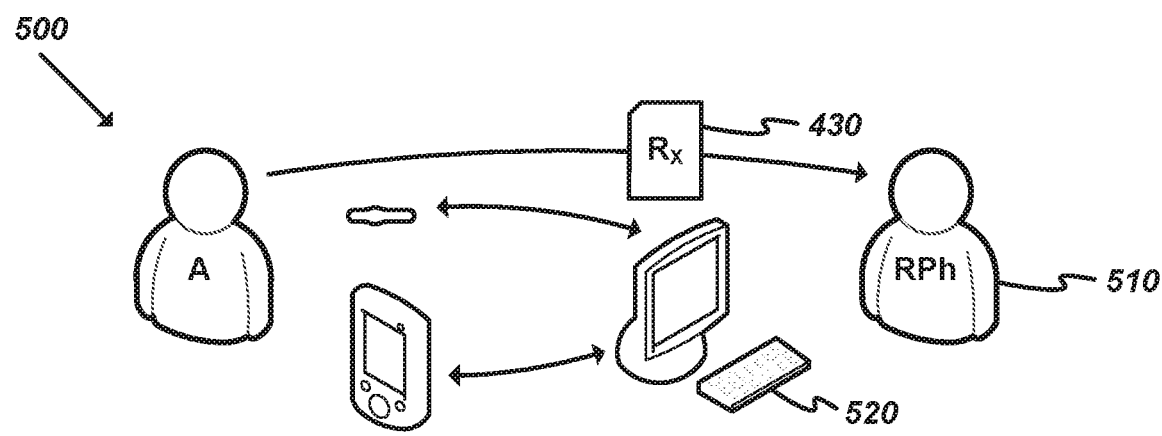
FIG. 5 illustrates a perspective view of the dosing system of FIG. 1 as used during a visit to a pharmacy.

FIG. 5 illustrates a perspective view of the dosing system 100 as used during a visit to a pharmacy. In this usage scenario 500, the patient 110 may visit a pharmacist or other provider 510. The provider may be associated with a device 520 (e.g., a mobile device, personal computer, workstation, medical device, etc.) that is able to interact with the dosing device 120 and/or the user device 130.

The prescription 430 may be utilized as is currently done. As above, future evolution may allow the prescription to be retrieved from the dosing device 120 or user device 130 (or from another resource such as a server of some embodiments). In addition, as will be described in more detail below, the pharmacist 510 may enable the device 120 (or usage thereof) in various appropriate ways. Relevant information (e.g., usage instructions, limitations, warnings, etc.) may be downloaded from device 520 to the dosing device 120 and/or user device 130. The dispensary device 520 may be associated with a docking station or other resource such that a dosing application or device interface is launched automatically when the dosing device 120 is coupled to the docking station (and/or otherwise coupled to the dispensary device 520).

Although the description below may refer to specific substance types (e.g., liquid solutions) and/or processing operations (e.g., heating the solution), one of ordinary skill in the art will recognize that various other substance types (e.g., powder) and/or processing operations (e.g., retrieving a measured amount) may be supported by and/or implemented using the device and system of some embodiments.

A first exemplary embodiment provides a smart dosing device comprising: a flow pathway comprising a cartridge receptacle that is able to house a cartridge; at least one sensor that captures identifying information related to the cartridge; a wireless communication module; and at least one security feature that restricts use of the smart dosing device.

A second exemplary embodiment provides a method of providing a measured dose using a smart dosing device, the method comprising: enabling dosing; measuring a provided dose; and disabling dosing.

A third exemplary embodiment provides a smart dosing system comprising: a smart dosing device having a unique identifier, the smart dosing device comprising a cartridge housing a substance, the cartridge having a unique cartridge identifier; and a server including a central database that stores usage information related to the smart dosing device, the usage information comprising: the unique identifier and the unique cartridge identifier.

Several more detailed embodiments are described in the sections below. Section I provides a description of a device architecture of some embodiments. Section II then describes a system architecture of some embodiments. Next, Section III describes methods of operation utilized by some embodiments. Lastly, Section IV describes a computer system which implements some of the embodiments.

I. Device Architecture

Figure 6:
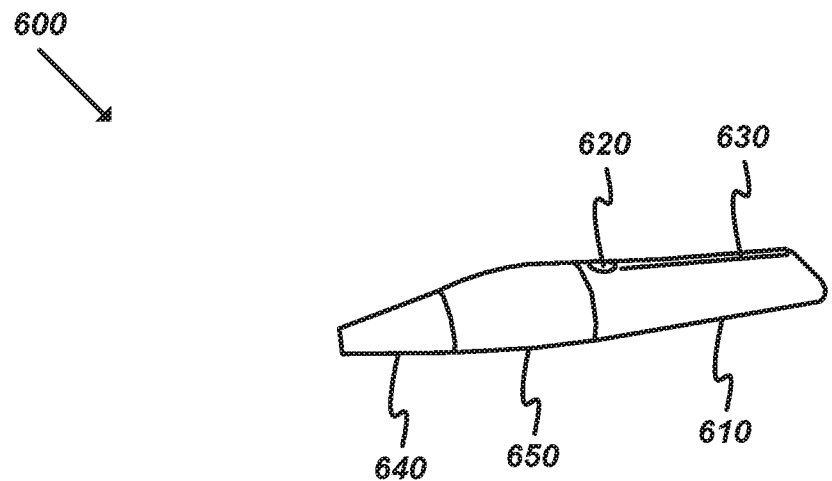
FIG. 6 illustrates a perspective view of a dosing device according to an exemplary embodiment.

FIG. 6 illustrates a perspective view of a dosing device 600 according to an exemplary embodiment. In this example, the dosing device may include a main body 610 having a single button control 620 and indicator feature 630, a mouthpiece 640, and a cartridge 650 or reservoir section.

Figure 7:
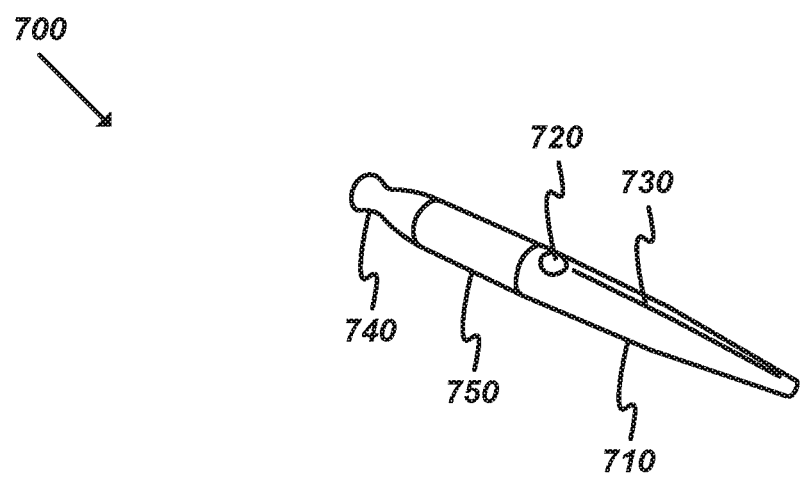
FIG. 7 illustrates a perspective view of an alternative dosing device according to an exemplary embodiment.

FIG. 7 illustrates a perspective view of an alternative dosing device 700 according to an exemplary embodiment. As shown, this example device may include a main body 710 with control 720 and indicator 730, mouthpiece 740, and cartridge or reservoir 750.

Different embodiments may include different specific features and/or elements depending on the type of substances being dispensed and/or attributes thereof. In this example, a user may activate the device by pressing the button 620 or 720 while receiving a dose via the mouthpiece 640 or 740. In some embodiments, the control 620 or 720 may include a scanner or other sensor that is able to compare captured data to reference data (e.g., fingerprint data) in order to authorize use.

The indicator 630 or 730 may light up, flash, change colors, and/or otherwise indicate various operation states or notifications (e.g., device is fully charged, device charging, battery low, dosing limit reached, authorization invalid, etc.). The cartridge 650 or 750, or portions thereof, may be disposable or refillable. A user or practitioner may be able to change and/or refill cartridges (or portions thereof) in order to access different substances, to continue usage through a multi-cartridge prescription, and/or other appropriate scenarios.

Figure 8:
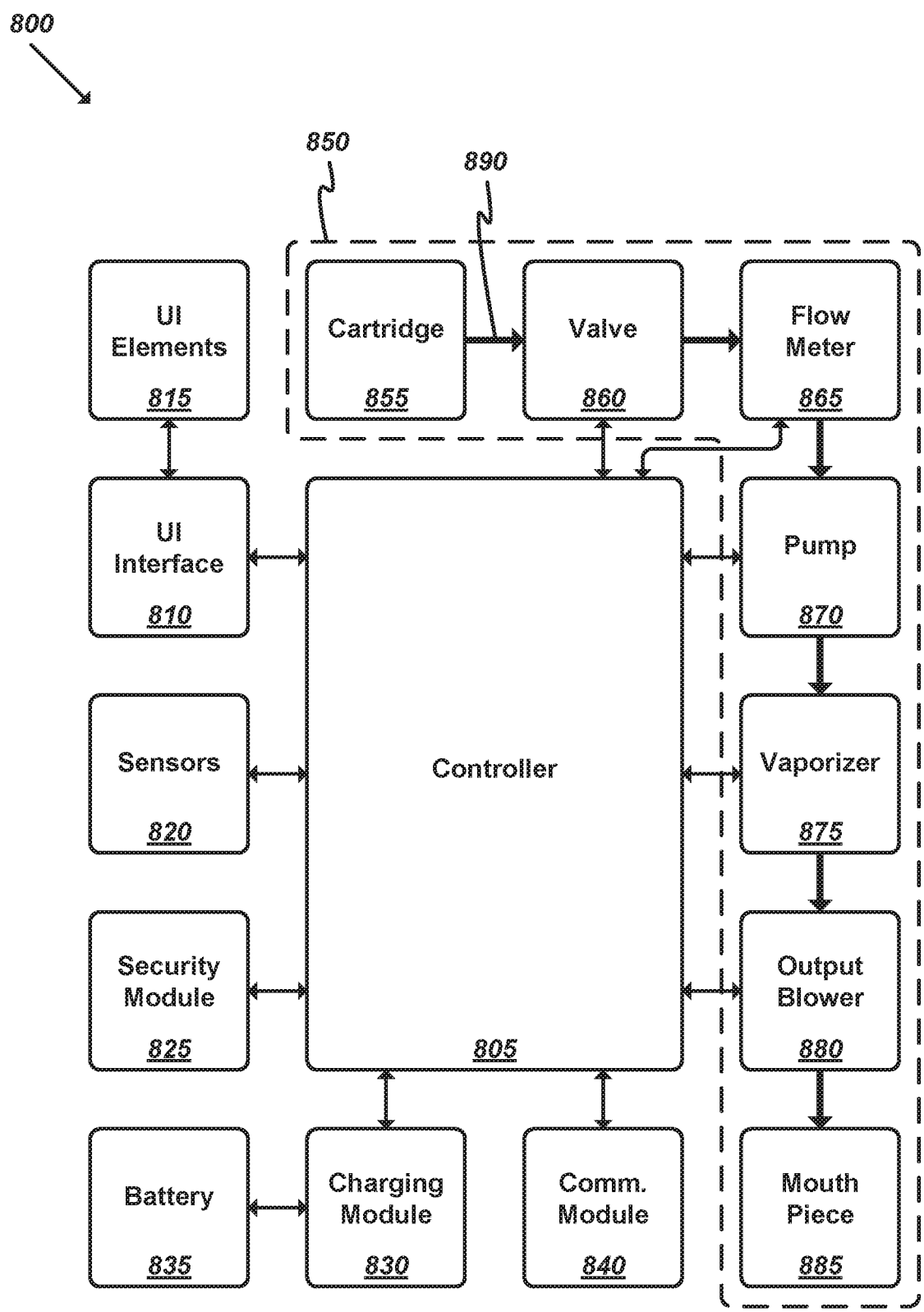
FIG. 8 illustrates a schematic block diagram of a dosing device according to an exemplary embodiment.

FIG. 8 illustrates a schematic block diagram of a dosing device 800 according to an exemplary embodiment. As shown, the device may include a controller 805, a user interface (UI) interface 810, various UI elements 815, sensors 820, a security module 825, a charging module 830, a battery 835, a communication module 840, and a substance delivery feature 850. Such a device may be utilized with vaporized inhaled substances.

The controller 805 may include a processor, microcontroller, other appropriate electronic devices, and/or other circuitry that is able to execute instructions and/or otherwise process data. The controller may be able to at least partly direct the operations of other device components. The controller may have an associated storage (not shown) that may be able to store instructions, data, etc.

The UI interface 810 may include various converters, drivers, etc. that are able to receive inputs from the UI elements 815 and/or send outputs to the UI elements. The UI interface 810 may receive outputs from, and send inputs to, the controller 805.

UI elements 815 may include various input and/or output elements. Examples of input elements include buttons, touchscreens, switches, dials, microphones, etc. Examples of output elements include displays, speakers, haptic feedback elements, etc. Some embodiments may include a touchscreen or other appropriate input/output elements. In addition to UI elements included in the device 800, some embodiments may utilize UI elements associated with connected user devices. For instance, a smartphone touchscreen may be used as an input/output element for the device 800.

Depending on the size and/or form factor of the device 800, the number of physical UI elements 815 included at the device 800 may be limited. For instance, some embodiments may include a single, multi-function button (e.g., press and hold to dispense the substance, press multiple times in succession to turn on/turn off, etc.). Of course, there is no limitation to appropriate UI elements that may be included (e.g., some embodiments may include a touchscreen, multiple buttons, a keypad, voice input and recognition, etc.).

Sensors 820 may include various electronic components that are able to quantify and/or capture various attributes associated with the device 800 and/or environment. Such sensors may include, for instance, cameras, NFC readers, graphic code readers, temperature sensors, location sensors, global positioning system (GPS) devices, movement sensors (e.g., accelerometers), etc. In some embodiments, the sensors 820 may include various components that are able to evaluate received signals (e.g., a bar code reader may utilize a camera to capture an image of the bar code, where the image is evaluated by some associated circuitry in order to extract data encoded in the bar code). The sensors may include various external components (e.g., location information may be retrieved from an associated user device). In some embodiments the sensors may include data retrieved from various network resources (e.g., environmental data such as temperature, humidity, etc. may be retrieved from a weather service based on location rather than measured directly by the device 800).

The security module 825 may manage use of the device 800. The module may interact with the controller 805 in order to identify security criteria associated with a dosing device and/or substance. In addition, the module 825 may utilize data retrieved from sensors 820, UI elements 815, and/or other appropriate components in order to implement various security protocols and/or algorithms. Operation of the security module will be described in more detail in reference to process 1900 below.

In some embodiments, the security module 825 may include security features related to management of the device 800. For instance, the security module 825 may include a unique identifier provided via a tag (e.g., a graphic code, NFC tag, etc.) such that use of the device 800 may be monitored or controlled.

The battery 835 may be a rechargeable or disposable power source that is able to store and provide power to the various device components. The charging module 830 may provide charging power to the battery 835, distribute power from the battery to other system components, and/or otherwise manage power consumption and/or distribution throughout the device 800. The charging module 830 may include wired (e.g., USB) and/or wireless interfaces (e.g., magnetic or inductive power couplings).

The communication module 840 may allow wired and/or wireless communication between the device 800 and various other appropriate devices and/or systems (e.g., user devices, servers, etc.). The communication module 840 may include various appropriate connectors (e.g., a USB port) and/or wireless pathways (e.g., Bluetooth, radio, etc.).

The substance delivery feature 850 may include a cartridge 855, a valve 860, a flow meter 865, a pump 870, a vaporizer 875, an output blower 880, a mouthpiece 885, and a flow pathway (or "supply pathway") 890. Together, such elements may extract the substance from the cartridge 855, vaporize or atomize the extracted substance, and provide the vaporized substance to a user via the mouthpiece. The flow pathway 890 may include various different cavities, conduits, etc. that may be arranged in various different ways. For instance, in some embodiments the cartridge 855 and mouthpiece 885 may be included in a single element that is able to be attached to device 800. Various example substance delivery features 850 are described in more detail in reference to FIG. 10-FIG. 13 below. The components of the delivery feature 850 other than the cartridge 855 may be collectively referred to as the "dosing module".

The substance delivery feature 850 may physically couple to the other elements of device 800 in various appropriate ways. For instance, some embodiments may include a complementary socket and receptacle such that the elements fit together physically. Such connections may also feature electrical connections using, for instance, pins and contact points, cables and connectors, wireless links, etc.

Returning to FIG. 8, the cartridge 855 may include a storage cavity for housing a substance, a channel, wick, and/or other appropriate pathway for extracting the substance, a coupling feature such that the cartridge may be able to be attached (and/or detached) from the device 800, and/or other appropriate features. The cartridge 855 (or portions thereof) may be reusable (i.e., refillable) or disposable. In some embodiments, the cartridge may include various components (e.g., a heating element, an atomizer, etc.) that are able to be controlled and/or otherwise utilized by device 800. The coupling feature may include mechanical elements (e.g., a threaded connector, a compression fit connector, etc.) and/or electronic elements (e.g., contacts, pins, etc.) that are able to engage complementary elements of the device 800.

The cartridge 855 may be removable and thus separate from the device 800. As such, the term "cartridge" may be used through this disclosure to refer to the cartridge 855 itself (i.e., a removable element having a storage cavity) and/or a cartridge receptacle associated with the device 800 (i.e., an attachment point, cavity, or other receptacle that is able to accept a cartridge 855). Some embodiments may include multiple cartridges.

The valve 860 may be an electronically controlled flow valve that may be able to either retain a substance within the storage cavity of the cartridge 855 or allow the substance to flow through the delivery feature 850. The valve 860 may communicate with the security features 950 and/or security module 825 such that vaporized substances are only dispensed when some security criteria are satisfied (e.g., when a matching fingerprint is present on a scanner).

The flow meter (or "measurement element") 865 may include various electronic elements that are able to quantify an amount of the stored substance that passes the meter (and/or is otherwise provided to the user). The flow meter may generate a signal that is provided to the controller 805. The controller may analyze the signal in order to determine an amount of substance consumed (e.g., by integrating the received signal).

In some embodiments, the measurement element 865 may detect a discrete quantity of items provided (e.g., a number of whole tablets or capsules provided). In some embodiments, the measurement element may detect a weight or volume of a provided substance. In some embodiments, the measurement element may be associated with a reservoir or storage cavity such that the amount (by weight, volume, percent of capacity, or other appropriate metric) of a stored substance may be measured before and after a dose is provided in order to determine the amount consumed.

The pump 870 may be a controllable pump that is able to move the substance along the flow path 890. The controller 805 may be able to define or control various attributes of pump operation (e.g., run time or activation period, speed or strength, etc.). The controller may analyze data received from the flow meter 865 in order to direct the operation of the pump 870. In some embodiments, the flow meter 865 may be omitted and a substance amount may be inferred based on run time (and/or other attributes) of the pump 870.

The vaporizer or atomizer 875 may be able to convert a substance from a liquid state to a gaseous or atomized state. The vaporizer may include various elements such as heating elements, agitation elements, etc. that are able to convert the substance appropriately for inhalation. In some embodiments, the vaporizer may mix the substance with other substances (e.g., air, water, etc.) which may be stored at the cartridge 855 and/or otherwise be available. The vaporizer 875 may be controller by controller 805 such that the vaporizer 875 only operates when the substance is being dispensed.

The output blower 880 may move the vaporized or atomized substance along the flow pathway 890. The output blower 880 may include fans, turbines, and/or other appropriate elements that are able to move the vaporized substance along the path 890. Some embodiments may omit the output blower 880 and/or conditionally operate the blower (e.g., based on user preferences or selections).

The mouthpiece 885 may include a conduit and appropriate fixtures that allow the vaporized or atomized substance to be provided to a user for inhalation. The mouthpiece may be removable. The mouthpiece may be made of various appropriate materials (e.g., metal, plastic, glass, etc.).

Different embodiments may provide different specific device housings and/or other form factor features. For instance, some embodiments may provide a cylindrical vaporizer where device electronics and battery are included at one end of the cylinder and a removable cartridge and mouthpiece may be attached at the opposite end of the cylinder. As another example, some embodiments may include a stationary or "desktop" housing, where elements are included in a box or similar structure that sits on a flat surface during use. Various elements may be attached to, or protrude from, the housing, such as tubes or other conduits, mouth pieces, etc. The housing and/or attachments may include various appropriate materials (e.g., plastic, metal, glass, silicone, rubber, etc.).

Figure 9:
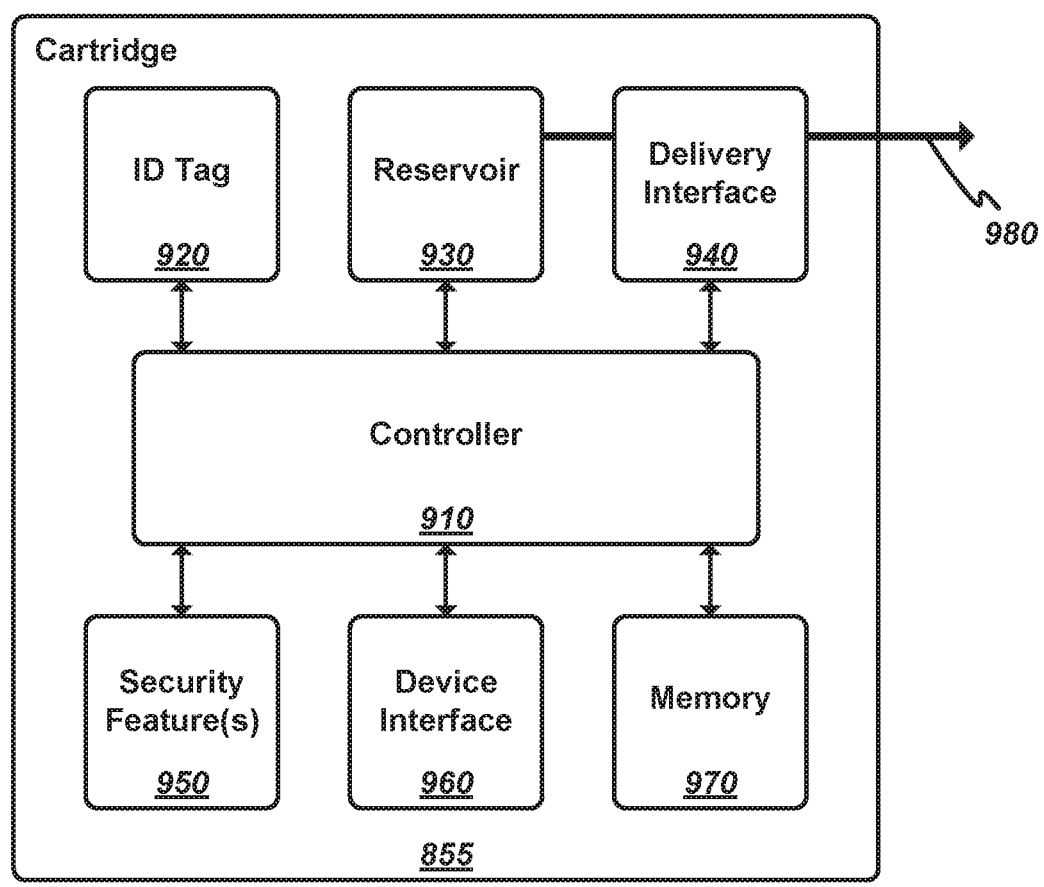
FIG. 9 illustrates a schematic block diagram of a cartridge included in some embodiments of the dosing device of FIG. 8.

FIG. 9 illustrates a schematic block diagram of a cartridge 855 included in some embodiments of the dosing device 800. As shown, the cartridge 855 may include a controller 910, an identification tag 920, a reservoir 930, a delivery interface 940, various security features 950, a dosing device interface 960, memory 970, and a substance delivery path 980.

The controller 910 may be able to at least partly control the operations of the other cartridge components 920-980. The controller 910 may be able to execute instructions and/or otherwise process data. Although the controller is shown as being part of the cartridge 855, the controller 910 may be located separately from the cartridge 855 but able to interact with the cartridge (e.g., through a wired connection or other physical link, through a wireless communication link, etc.).

The identification tag 920 may include a unique cartridge identifier (e.g., a serial number) that is able to be retrieved by other elements of device 800, such as sensors 820 or security module 825. Likewise, device 800 may be associated with a unique identifier. In some embodiments, the identification tag 920 may broadcast the unique ID via a transmitter (e.g., radio, Bluetooth, etc.). The identification tag may be a passive element in some embodiments, such that the unique ID may be read by other element (e.g., using NFC).

The reservoir 930 may include a cavity, vessel, or other appropriate housing for a particular substance or substance type (e.g., liquid, powder, capsule, etc.). The reservoir may generally be a passive element, whereby a substance is retained absent interference from another device element (e.g., until extracted through the delivery interface 940). In some embodiments, the reservoir 930 may include (or be associated with) various local environmental sensors (e.g., temperature sensors, humidity sensors, pressure sensors, etc.) that may provide sensed data to the controller 910 or other components. Such data may be utilized to ensure the stored substance is still viable or effective. In some embodiments, the reservoir 930 may be associated with one or more sensors that are able to quantify an amount of substance retained in the reservoir. Such an amount may be specified as an absolute value (e.g., "1 mg remaining" or "3 doses remaining") or a relative amount (e.g., "25% full").

The delivery interface 940 may include various valves, pumps, conduits, latches, actuators, etc. as may be used to move the stored substance from the reservoir 930 and through the delivery path 980 such that the substance may be provided to an appropriate delivery feature interface element (e.g., valve 860). The delivery interface 940 may communicate with the security features 950 and/or security module 825 such that stored substances are only dispensed when some security criteria are satisfied (e.g., when a matching fingerprint is present on a scanner).

The security features 950 may include various physical locks or features (e.g., latches, electronic locks, mechanical locks, tamper-proof containers, etc.) and/or various electronic or electro-mechanical features (e.g., audio or visual alarms, lock controllers, breach detection elements, etc.). Such security features may generally prevent use of the associated substance until satisfaction of some security criteria (e.g., verifying user biometric data, matching a user to a prescription, validating a cartridge versus a prescription, etc.). For instance, some embodiments may enclose the cartridge 855 (or portions thereof) in a steel "bullet".

The dosing device interface 960 may include various physical and/or electronic connecters that may couple a main body of the dosing device 800 to the cartridge 855. The interface 960 may generally allow the device 800 to retrieve cartridge information (e.g., unique identifier, remaining amount of the stored substance, etc.).

The memory 970 may include information related to the cartridge and/or usage thereof. In some embodiments, the memory may be integrated with the ID Tag 920 or other cartridge components. In general, the memory 970 may include information related to the substance, the cartridge, the usage device(s), user information, dosing information (e.g., amount, schedule, etc.), and/or other relevant information (e.g., location, security information, etc.).

The substance delivery path 980 may include various conduits, valves, connection ports, etc. that allow the substance to move from the reservoir to the delivery feature interface (e.g., valve 860). The path 980 may terminate at a connection port that is able to securely couple the cartridge 855 to the delivery feature interface.

One of ordinary skill in the art will recognize that the cartridge 855 may be implemented in various different ways without departing from the scope of the disclosure. For instance, various components may be omitted, other components included, and/or the components may be arranged in different configurations. As one example, in some embodiments the cartridge 855 may include only a tag 920, a substance reservoir 930 and a feeder 940. As another example, some embodiments may divide the cartridge into a set of disposable elements and a set of re-usable elements. For instance, the ID tag 920, reservoir 930, and deliver interface 940 may be included in a disposable portion of the cartridge 855, while the other elements may be included in a re-usable portion of the cartridge in order to lower the cost of the disposable portion.

In some embodiments, the entire device 800 may be disposable (or not intended for re-use). In other embodiments, every component of the device 800 may be refillable and/or otherwise re-usable.

Figure 10:
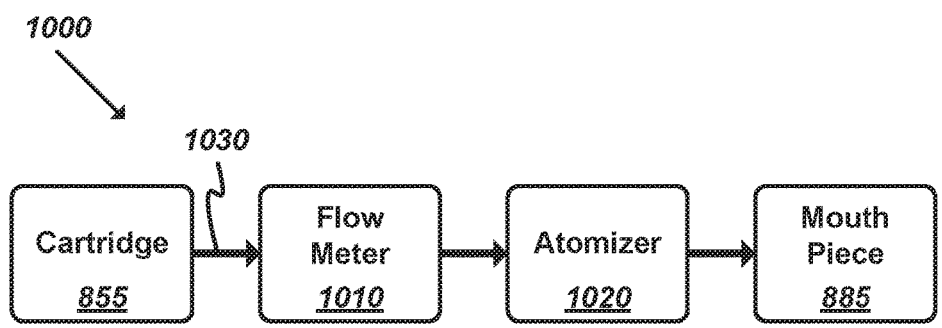
FIG. 10 illustrates a schematic block diagram of a substance delivery feature included in some embodiments of the dosing device of FIG. 8.

FIG. 10 illustrates a schematic block diagram of a substance delivery feature 1000 included in some embodiments of the dosing device 800. The delivery feature 1000 may be associated with substances delivered as an atomized spray. As shown, the delivery feature may include cartridge 855, a flow meter 1010, an atomizer 1020, and mouthpiece 885.

The cartridge 855 and mouthpiece 885 were described above.

The flow meter 1010 may be similar to flow meter 865 described above. In this example, the flow meter 1010 may measure liquid received from the cartridge 855. In some embodiments, the flow meter 1010 may be located such that the output of the atomizer 1020 is measured.

The atomizer 1020 may include various mechanical features (e.g., nozzles, pumps, conduit, etc.) and/or electrical or electronic features (e.g., a heating coil as used in a vape tank). The atomizer may be able to emit liquid as a fine spray. Such liquid may be retrieved from cartridge 855 via flow meter 1010. The atomizer 1020 may communicate with the security features 950 and/or security module 825 such that atomized spray is only dispensed when some security criteria are satisfied (e.g., when a matching fingerprint is present on a scanner).

During use, a liquid substance may flow along pathway 1030 from the cartridge 855, through flow meter 1010 and into atomizer 1020. The atomizer may convert the liquid into a fine spray which continues along pathway 1030 through mouthpiece 885, where the atomized substance is delivered to a user.

Figure 11:
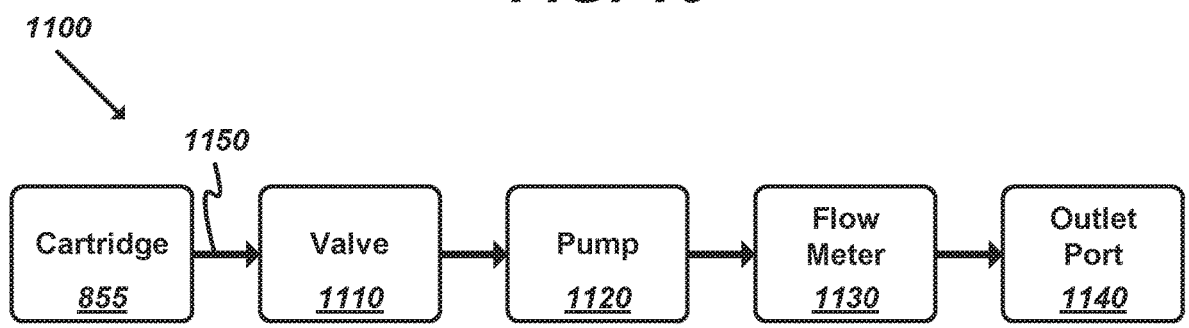
FIG. 11 illustrates a schematic block diagram of an alternative substance delivery feature included in some embodiments of the dosing device of FIG. 8.

FIG. 11 illustrates a schematic block diagram of an alternative substance delivery feature 1100 included in some embodiments of the dosing device 800. The delivery feature 1100 may be associated with substances delivered in liquid form. As shown, the delivery feature may include cartridge 855, a valve 1110, a pump 1120, a flow meter 1130, and an outlet port 1140.

The cartridge 855 was described above.

The valve 1110 may be similar to valve 860. Valve 1110 may be able to control the flow of liquid substances out of the cartridge 855. The valve may communicate with the security features 950 and/or security module 825 such that liquid is only dispensed when some security criteria are satisfied (e.g., when a matching fingerprint is present on a scanner).

The feature 1100 may allow medication to be dispensed and mixed with other liquids (e.g., water, orange juice, etc.) or semi-solid foods (e.g., applesauce, pudding, etc.). Thus, the dosing device 800 may act as an electronically controller dropper.

The pump 1120 may be similar to pump 870 described above. The pump 1120 may be able to move liquids along the flow pathway 1150.

Flow meter 1130 may be similar to flow meter 865 described above. The flow meter 1130 may be able to measure volumes of liquid that move along pathway 1150.

The outlet port 1140 may include various appropriate physical and/or mechanical features that may allow a user to dispense a measured dose of a liquid substance. In some embodiments, the outlet port may simply be an opening at the end of pathway 1150 that allows the liquid to be dispensed into a mixing vessel. Some embodiments may include a mouthpiece or similar feature for dispensing a liquid directly into the mouth of a user. Some embodiments may include specialized delivery features (e.g., a "paddle" for releasing liquid under the tongue).

During use, a liquid substance may flow along pathway 1150 from the cartridge 855, through valve 1110, through pump 1120, through flow meter 1130 and out of outlet port 1140.

Figure 12:
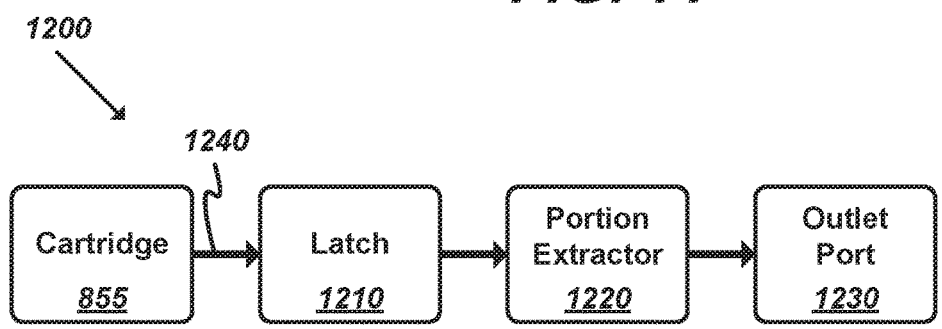
FIG. 12 illustrates a schematic block diagram of a second alternative substance delivery feature included in some embodiments of the dosing device of FIG. 8.

FIG. 12 illustrates a schematic block diagram of a second alternative substance delivery feature 1200 included in some embodiments of the dosing device 800. The delivery feature 1200 may be associated with substances delivered in powdered form. As shown, the delivery feature may include cartridge 855, a latch 1210, a portion extractor 1220, and an outlet port 1230.

The cartridge 855 was described above.

The latch 1210 may be a mechanical or electro-mechanical feature that controls flow of the powdered substance from the cartridge 855. The latch 1210 may include features such as a spring hinge, door or flap, seals or gaskets, a rotating disk with a dispensation opening, etc. The latch may communicate with the security features 950 and/or security module 825 such that the powdered substance is only dispensed when some security criteria are satisfied (e.g., when a matching fingerprint is present on a scanner).

The portion extractor 1220 may include a cavity or receptacle that is able to hold a measured dose of the powdered substance. In some embodiments, the portion extractor may be controllable such that the measured dose is able to be configured for each particular usage scenario. For example, the portion extractor may have multiple cavities of differing sizes, each associated with a different dose amount. As another example, the portion extractor may have a movable feature (e.g., a sliding floor or wall of a cavity) that is able to change the capacity of the extractor. As still another example, some embodiments may utilize scales or other measuring features (e.g., one or more flow meters) to measure and retrieve a specified amount of the substance, up to the full capacity of the extractor (i.e., the amount may be limited by the capacity of the extractor cavity).

The outlet port 1230 may include various appropriate physical and/or mechanical features that may allow a user to dispense a measured dose of a powdered substance. In some embodiments, the outlet port may simply be an opening at the end of pathway 1240 that allows the powder to be dispensed into a mixing vessel. Some embodiments may include a mouthpiece or similar feature for dispensing a powder directly into the mouth of a user.

During use, an amount of powdered substance may be moved along pathway 1240 from the cartridge 855, through the latch 1210, through the portion extractor 1220, and out of outlet port 1230.

Figure 13:
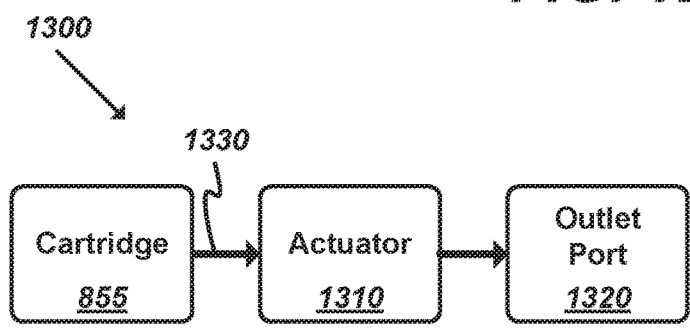
FIG. 13 illustrates a schematic block diagram of a third alternative substance delivery feature included in some embodiments of the dosing device of FIG. 8.

FIG. 13 illustrates a schematic block diagram of a third alternative substance delivery feature 1300 included in some embodiments of the dosing device 800. The delivery feature 1300 may be associated with substances delivered through tablets, capsules, or other discrete consumables. As shown, the delivery feature may include cartridge 855, an actuator 1310, and an outlet port 1320.

The cartridge 855 was described above. In this example, the cartridge may include a magazine, cassette, or other feeder that is able to store multiple tablets (or other similar discrete substance form). The feeder may include an outlet where, as each tablet is removed, the next tablet is pushed along to take the place of the delivered tablet. Such a feeder may utilize features such as springs, latches, guides, etc.

The actuator 1310 may include various electro-mechanical features that allow a single tablet (or other discrete form) to be extracted from the cartridge 855. The actuator 1310 may also move the tablet along the flow path 1330 such that it is provided to a user for consumption through the output port 1320. The actuator 1310 and/or other appropriate features may act as a latch to securely store discrete consumables until provided for use. The actuator may communicate with the security features 950 and/or security module 825 such that discrete consumables are only dispensed when some security criteria are satisfied (e.g., when a matching fingerprint is present on a scanner).

One of ordinary skill in the art will recognize that the dosing device of some embodiments may be implemented with various other delivery features as appropriate for various other substance types and/or delivery methods (e.g., syringes and injected substances, applicators and topical creams or ointments, etc.). Furthermore, the device of some embodiments is customizable such that newly developed substances and delivery methods may be easily implemented.

In addition, the various components may be arranged in different orders (e.g., a flow meter may be placed before or after a pump). Furthermore, even though the pathways may be described as going through various components, the pathways may, in fact, traverse paths nearby or adjacent to such components (e.g., the flow meter may be situated alongside a conduit or other component such as a pump).

During operation, a user may activate the device 800 (e.g., by pressing a button or other UI element 815) and inhale the vaporized substance. The device 800 may store usage information (e.g., amount, time of day, etc.) for provision to other system elements as described below in reference to FIG. 14. Operation of the device 800 will be described in more detail in reference to FIG. 15-FIG. 25 below.

One of ordinary skill in the art will recognize that device 800 may be implemented in various different ways without departing from the scope of the disclosure. For instance, some embodiments may omit various elements (e.g., UI elements, wireless communication elements, etc.). Some embodiments may include additional elements. In addition, the various elements may be arranged in different ways with different communication pathways and/or different flow pathways.

II. System Architecture

Figure 14:
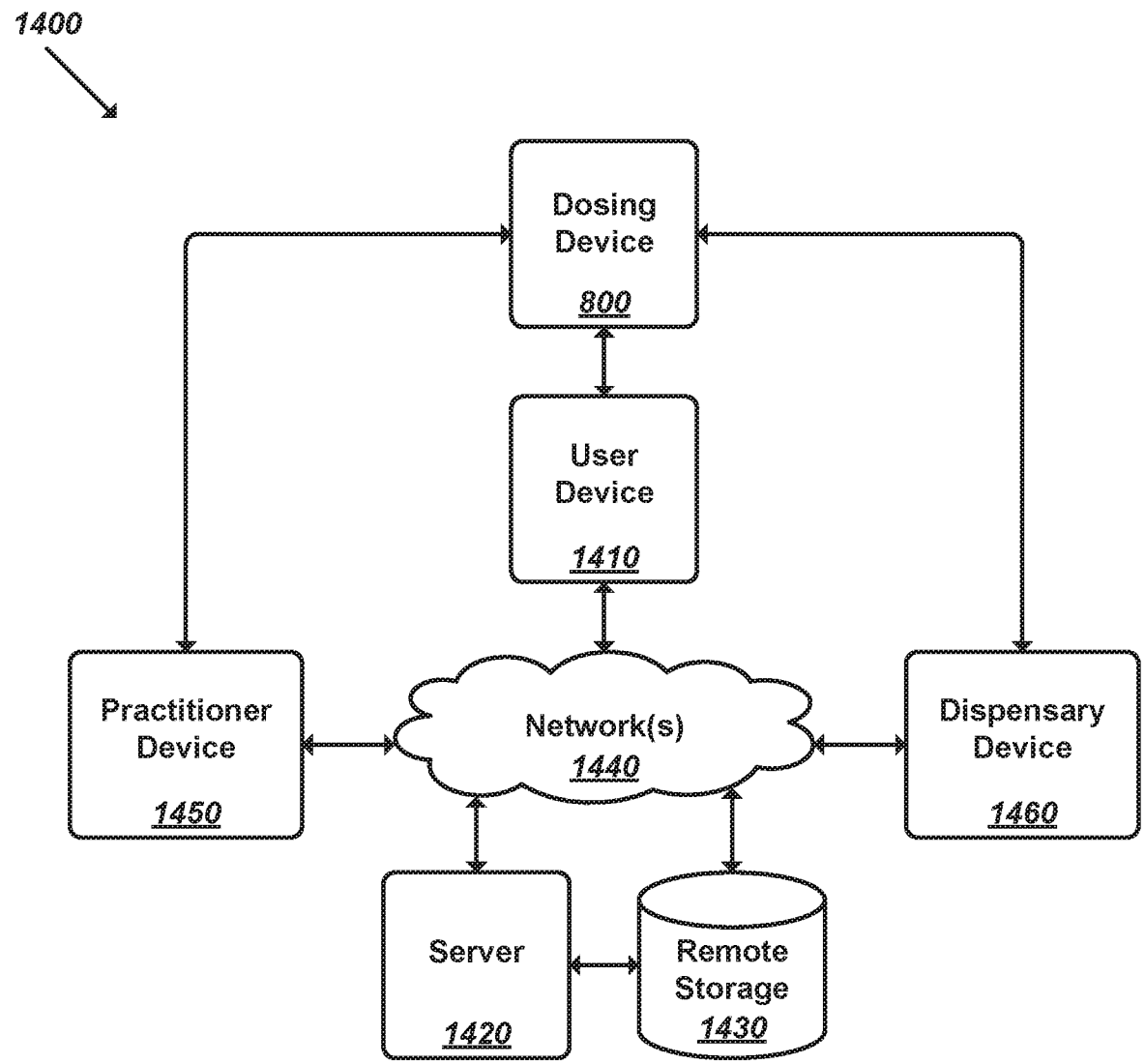
FIG. 14 illustrates a schematic block diagram of a system that includes the dosing device of FIG. 8.

FIG. 14 illustrates a schematic block diagram of a system 1400 that includes the dosing device 800. As shown, the system 1400 may include the dosing device 800 described above, one or more user devices 1410, one or more servers 1420, one or more remote storages 1430, and a set of networks 1440.

Each user device 1410 may be an electronic device such as a smartphone, tablet, personal computer, wearable device, medical device or terminal, etc. The user device may be able to be communicatively coupled to the dosing device 800 (e.g., using module 840) via a wired or wireless channel. The user device 1410 may be able to connect to various networks 1440. In some embodiments, the dosing device 800 may be able to connect directly to networks 1440 without any user device 1410.

Each server 1420 may be an electronic device capable of executing instructions and/or otherwise processing data. Servers may be associated with various types of entities or users. For instance, a cartridge manufacturer may have a server that is able to provide information related to cartridges and/or collect information related to use. As another example, a group of medical practitioners such as doctors, nurses, administrators, etc. may be associated with an entity such as a hospital or health care network that maintains a server related to patients or clients of the entity. In some cases, one or more servers may be operated by a government or other official agency.

As still another example, a server may be associated with a platform or other appropriate resource that is able to link various users and/or groups of users. For instance, a patient user may be able to create an account, collect usage data associated with the account, and provide the data to various other parties (e.g., a doctor, pharmacist, manufacturer, distributor, etc.). Such data may be provided anonymously, as appropriate, for use in various studies, trials, etc.

Each remote storage 1430 may be an electronic device that is able to store instructions and/or data. Such a storage may be accessed via an associated server 1420 or via a resource such as an application programming interface (API). The storages 1430 may be able to receive data from the various other system resources and/or provide data to those resources, as appropriate.

The set of networks 1440 may include various wired and/or wireless communication pathways, such as Ethernet, cellular networks, Wi-Fi networks, the Internet, etc.

The practitioner device 1450 may be an electronic device such as a personal computer, workstation laptop, etc. that may be associated with one or more practitioners, facilities, etc. The practitioner device may be able to communicate directly and/or indirectly with other system elements. For instance, the practitioner device may communicate with the dosing device 800 over a wired communication link or a local wireless channel. As another example, the practitioner device 1450 may be able to communicate with the server 1420, the patient user device 1410, and the dispensary device 1460 across network 1440. In some embodiments, the dosing device 800 may be able to connect to network 1440. Alternatively, data may be retrieved from (or provided to) user device 1410 which may, in turn, communicate with the other system elements available across network 1440.

The dispensary device 1460 may be an electronic device similar to practitioner device 1450. The dispensary device 1460 may be associated with one or more individual dispensers, dispensaries, pharmacies, etc.

In some embodiments, practitioners and/or dispensers may be associated with additional devices (and/or different devices) than those shown. For instance, each practitioner and/or each dispenser may be associated with a smartphone or tablet that is able to be associated with the system 1400. Such devices may interact with devices 1450-1460 in order to access system 1400 or they may access the system directly via network 1440 (with appropriate validation and authentication).

Devices 1450-1460 may implement various security features, such as validating user credentials through a username and password login process, scanning biometric information such as a fingerprint, etc.

The system of some embodiments may include similar servers and/or other devices linked to other user types or entities. For instance, such devices may be associated with insurance providers, device manufacturers or distributors, cartridge manufacturers or distributors, substance manufacturers or distributors, government or other oversight agencies, medical facilities, dispensary or pharmacy networks, etc.

The various devices may each execute dedicated software of some embodiments to implement various system features. For instance, a practitioner may monitor patient usage through such software. As another example, a pharmacy may disable a dosing device through such software based on suspicious usage information received through such software. As still another example, a government agency may monitor physician behavior by analyzing patient usage patterns or suspected misuse through such software.

Each user and/or entity may be associated with uniquely identifying information (e.g., a serial number, username, etc.) that allows data to be collected regarding each entity, links to be formed among entities, and/or other enable monitoring and analysis at an individual level. For instance, every delivered dose may be stored as a database entry that includes a reference to a specific user, device, cartridge, manufacturer, prescription, physician, pharmacist, etc. in addition to dosing data or other usage information.

One of ordinary skill in the art will recognize that system 1400 may be implemented in various different ways without departing from the scope of the disclosure. For instance, some embodiments may omit various components (e.g., remote storages, servers, etc.). Some embodiments may include additional elements (e.g., external charging devices). In addition, the various elements may be arranged in different ways with different communication pathways.

III. Methods of Operation

Figure 15:
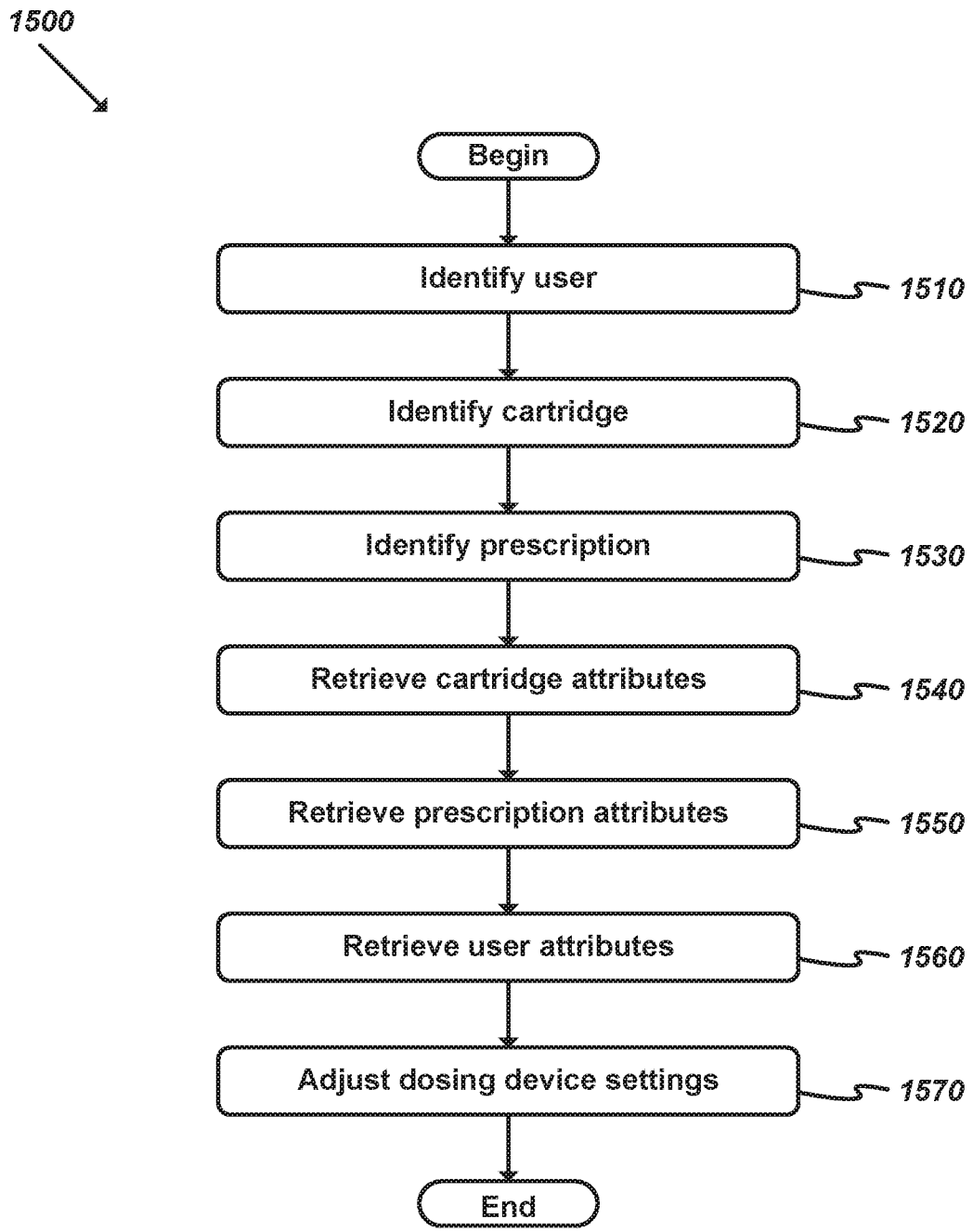
FIG. 15 illustrates a flow chart of an exemplary process that initializes the dosing device of FIG. 8.

FIG. 15 illustrates a flow chart of an exemplary process 1500 that initializes the dosing device 800. Such a process may be executed by the dosing device in some embodiments. In addition, various operations may be performed by a resource such as user device 1410 or server 1420, where such resources may execute applications associated with the device of some embodiments. The process may begin, for instance, when a dosing device is powered on, when a new cartridge is coupled to the device, after a user reset, after the battery is charged, etc.

As shown, the process may identify (at 1510) a user of the device 800. The user may be identified in various appropriate ways, depending on the circumstances. For instance, the device may have been previously associated with a user account using an application of some embodiments. Such account data may be stored at the device itself and/or retrieved from an external resource such as a user device or server. As another example, the first time a device is powered on or otherwise used, the user may be prompted to enter identifying information (e.g., name, username, etc.) that may be used to identify the user in the future. As still another example, some usage may be anonymous and no user information may be identified or otherwise procured.

Next, the process may identify (at 1520) the cartridge 855. Such identification may include attributes such as a cartridge type, serial number, etc. The identification may utilize sensors 820. Different embodiments may use different identification algorithms and/or features. For instance, some embodiments may include NFC tags and readers. As another example, some embodiments may utilize graphic codes and optical devices (e.g., cameras, bar code readers, scanners, etc.). In some embodiments, a resource external to the device 800 may be utilized. For instance, a camera included in a user device 1410 may be used to scan a graphic code.

An application running on the user device may decode the scanned information and identify the cartridge. As another example, an application running on the user device may provide a list of options and a user may select the appropriate cartridge. As still another example, the cartridge 855 may include circuitry that may be read by the device 800 to retrieve a serial number, type, and/or other identifying information. As above, in some usage scenarios, the cartridge may not be identified.

Process 1500 may then identify (at 1530) a prescription associated with the user and/or cartridge, if appropriate. The prescription may be identified via an external resource such as user device 1410, server 1420, and/or storage 1430. For instance, a request may be sent from the device, via the user device 1410 to a server 1420. The request may include information associated with the user and/or cartridge. A response may include a serial number or other identifying information related to the prescription. In some embodiments, user inputs may be received that indicate usage is related to a prescription (or that usage is not associated with a prescription).

Next, the process may retrieve (at 1540) attributes associated with the cartridge identified at 1520. Such attributes may include identifying information (e.g., type, serial number, etc.), usage information (e.g., environmental limitations, vaporizing attributes such as temperature, voltage or current range, etc.), substance information (e.g., volume, concentration, etc.), security information (e.g., prescription requirements, age or demographic requirements, etc.), and/or other appropriate information. If no cartridge was identified (at 1520), various default attributes may be used.

The process may then retrieve (at 1550) prescription attributes, if a prescription was identified. Such prescription attributes (and/or other usage instructions) may include, for instance, dose amount, dose frequency, maximum dose, maximum dose over time, total usage period, etc. In some embodiments, the prescription attributes may be manually entered by a user.

Process 1500 may then retrieve (at 1560) attributes associated with the user. Such attributes may include, for instance, biometric information (e.g., age, gender, height, weight, etc.), condition information, user preferences, etc. As above, such attributes may be entered manually. If no user-specific information is available, default values may be used.

Next, the process may adjust (at 1570) the dosing device settings based on the retrieved data and then may end. Such adjustments may include storage of parameter values at the dosing device 800. The settings may be related to any module (or set of modules) described above in reference to FIG. 8.

Figure 16:
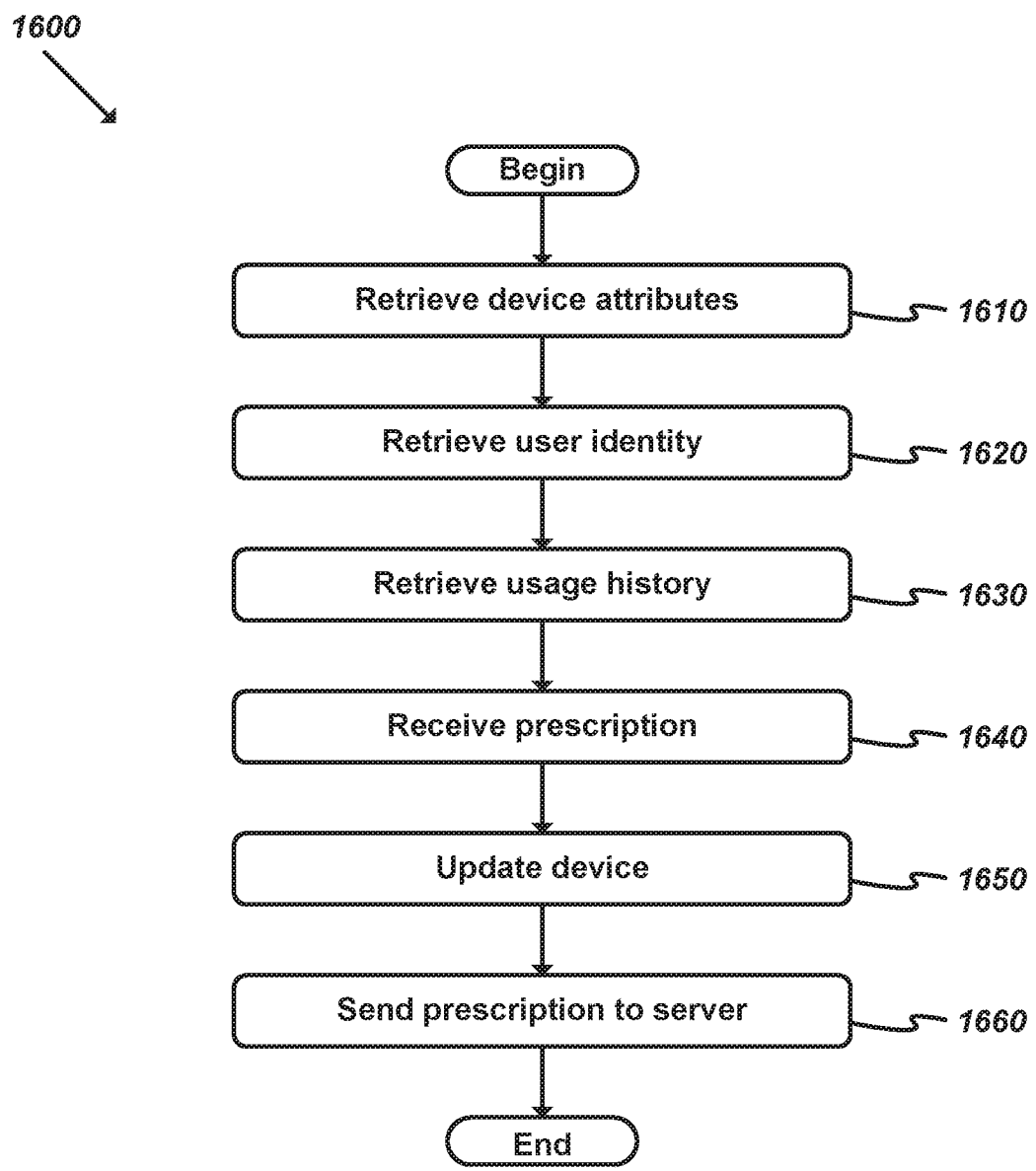
FIG. 16 illustrates a flow chart of an exemplary prescription process that utilizes the dosing device of FIG. 8.

FIG. 16 illustrates a flow chart of an exemplary prescription process 1600 that utilizes the dosing device 800. Such a process may be performed by a resource such as practitioner device 1450. The dosing device 800, user device 1410, and/or server 1420 may execute complementary processes. Process 1600 may utilize an application or other dedicated software running on device 1450. The process may update a prescription associated with a user and dosing device.

As shown, the process may retrieve (at 1610) device attributes. Such attributes may be retrieved through a wired or wireless connection between the practitioner device 1450 and the dosing device 800. Device attributes may include, for instance, a serial number or other device identifier, model or device capability information, and/or other relevant information regarding the device. For instance, some devices may include attributes (e.g., a portion of the serial number) that indicate supported substance types (e.g., liquid, powder, etc.). As another example, some device attributes may indicate connector type, size, etc. such that cartridges or delivery features having complementary components may be prescribed.

Next, the process may retrieve (at 1620) a user identity of a user associated with the device 800. Such an identity may be retrieved from information stored on the device 800, information received from a user device 1410, identification based on biometric evaluation, identification based on manual verification (e.g., the practitioner may verify a physical ID card), and/or other appropriate ways. The user identity may be specified using a serial number or other anonymizing reference such that the personal information of the user is protected.

Process 1600 may then retrieve (at 1630) usage history. Such usage history may include, for instance, an entry for each usage session that includes an amount of dose provided, a timestamp indicating when dose was provided, user verification information (e.g., a captured image of a fingerprint scan), etc. Usage history may be retrieved via user device 1410 or directly from the dosing device 800.

The process may then receive (at 1640) a prescription. The prescription may be provided by the practitioner through the device 1450. The prescription may indicate various relevant attributes associated with the device of some embodiments, in addition to specifying standard dose and scheduling instructions. For instance, the prescription may indicate a specific cartridge type or model that is appropriate for the dosing device, the prescribed substances, or other relevant factors (e.g., user preferences, user age or capacity, etc.).

Next, the process may update (at 1650) the dosing device with information related to the prescription (e.g., dose amounts, schedule, etc.). In some embodiments, a signed digital copy (or other certified or authenticated version) of the prescription may be uploaded to the dosing device.

Process 1600 may then send (at 1660) the prescription to the server 1420 and then may end. The prescription sent to the server may include similar information as that sent to the dosing device 800 and may further include information related to the user identity.

Figure 17:
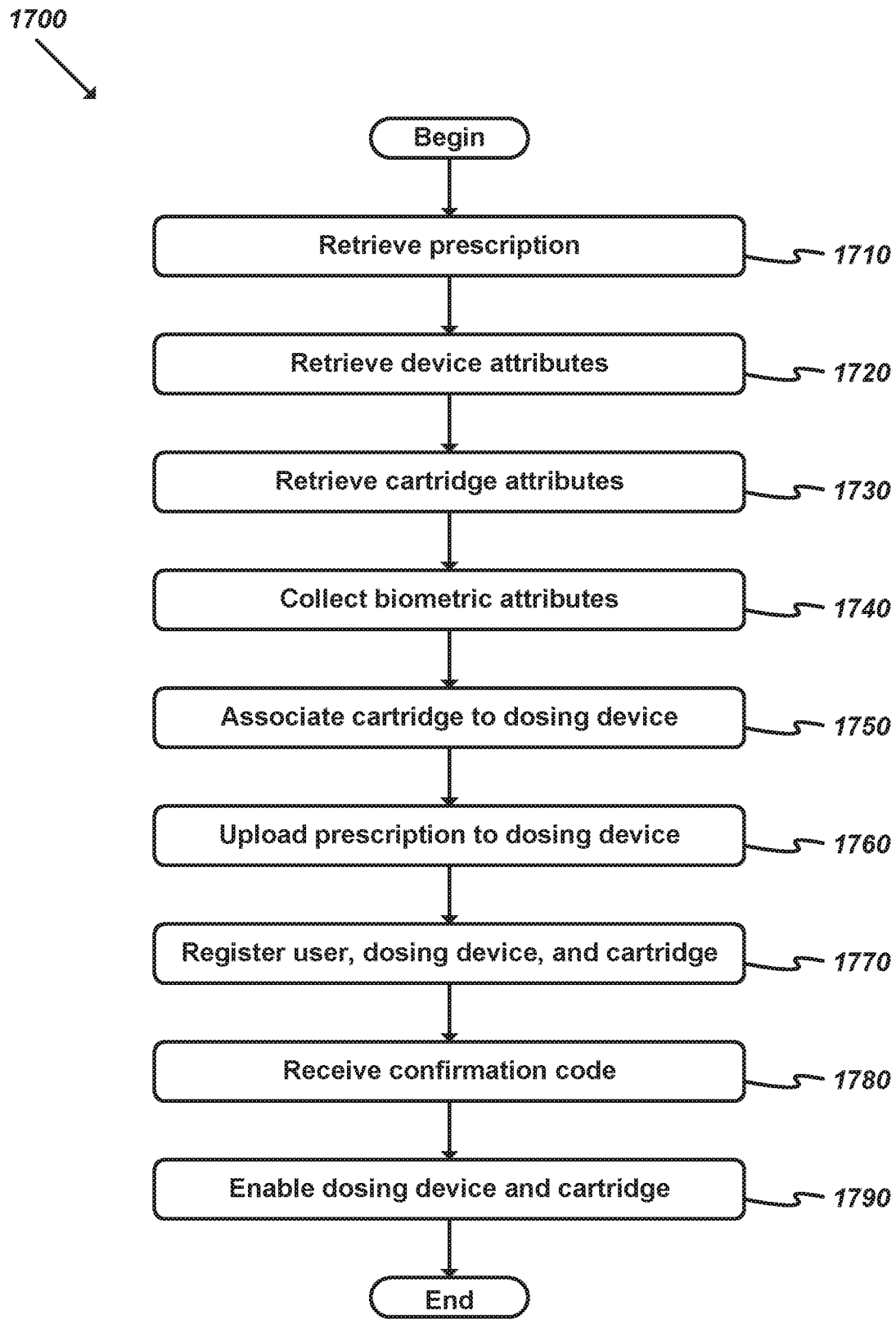
FIG. 17 illustrates a flow chart of an exemplary prescription fulfillment process that utilizes the dosing device of FIG. 8.

FIG. 17 illustrates a flow chart of an exemplary prescription fulfillment process 1700 that utilizes the dosing device 800. Such a process may be performed by a resource such as dispensary device 1460. The dosing device 800, user device 1410, and/or server 1420 may execute complementary processes. Process 1700 may utilize an application or other dedicated software running on device 1460. The process may enable use of a prescription by dosing device 800.

As shown, the process may retrieve (at 1710) a prescription. Such retrieval may be performed in various appropriate ways, where a particular method may be selected based on applicable regulations. In some embodiments the dispensary device 1460 could retrieve the prescription from user device 1410 or delivery device 800 over a wired or wireless communication link. As another example, the prescription may be retrieved manually (e.g., as a handwritten paper document) by the pharmacist from the patient. In some embodiments, the prescription information may be downloaded from server 1420 to dispensary device 1460.

Process 1700 may then retrieve (at 1720) device attributes. Such attributes may be retrieved by the dispensary device 1460 from the user device 1410 or dosing device 800. The attributes may include information related to the dosing device such as serial number, type or model, supported substance types, etc. In some embodiments, the dispensary device 1460 may download dosing device information from server 1420, based on the dosing device serial number, type, etc.

In some cases, a new patient may not yet have a dosing device 800. The device may be selected based on analysis of the prescription, comparison of the prescription requirements to capabilities of available devices, provider preference, user preference, etc.

The process may then retrieve (at 1730) cartridge attributes. The cartridge itself may be selected by a pharmacist or other provider, based on the prescription. In some embodiments, a cartridge 855 may be automatically retrieved based on the prescription (e.g., the prescription may be retrieved from the dosing device 800, used to identify the appropriate cartridge based on information retrieved from server 1420, and a cartridge matching that specified by the prescription may be automatically retrieved from inventory and provided via a resource such as a secure vending station). The cartridge attributes may be retrieved by the dispensary device 1460 from the cartridge 855. Alternatively, the dispensary device 1460 may include a scanner, reader, or other appropriate element that allows the device to retrieve information provided by the ID tag 920, which may be used, in turn, to retrieve cartridge information from a resource such as server 1420.

Next, process 1700 may collect (at 1740) biometric attributes related to the patient. Such attributes may include, for instance, photographic data (e.g., facial photos, retinal, fingerprint, or other physical scans, etc.). The attributes may be selected for maximum security such that an unauthorized user is not able to activate the dosing device 800. Different embodiments may collect various different attributes.

As an alternative to biometric data, some embodiments may utilize various other authentication algorithms. For instance, in some embodiments a password may be needed to authorize use. As another example, a local connection to an authorized user device may be needed to enable dosing device use. Some embodiments may utilize multiple methods to authenticate users before authorizing use of a dosing device.

The process may then associate (at 1750) the cartridge to the dosing device. Such association may be performed in various different ways, depending on various relevant factors. For instance, device information such as a serial number may be uploaded to cartridge memory 970 and the cartridge security features 950 may verify that the serial number in memory matches the dosing device 800 in which the cartridge 855 is currently installed. Similarly, the cartridge ID may be uploaded to the dosing device 800 and the dosing device may verify that the currently installed cartridge has a matching ID. Some embodiments may require a physical key or tool to associate the cartridge to the device (e.g., a pharmacist or other registered provider may be able to unlock a secure compartment or connection port that enables connection of the cartridge to the device and may even "lock" the cartridge to the device such that tampering or removal is prevented or detectable). Some embodiments may utilize a digital key or password to associate the cartridge to the device, such that the proper code must be entered to electronically unlock the cartridge or device for use.

Process 1700 may then upload (at 1760) the prescription to the dosing device. Such information may be uploaded automatically from the dispensary device 1460, if available. In some embodiments, the paper prescription may be manually entered by the pharmacist for upload to the dosing device. The prescription may be provided to the device in various appropriate formats and may depend on the specific substance type, attributes, dosing levels, and/or other relevant factors. For instance, some embodiments may include a complete schedule for use of the entire contents of a cartridge 855 (e.g., by including a table or listing of dose times and amounts based on the initialization time). As another example, some embodiments may specify an amount of a single dose and a maximum amount to be provided over a specified time period.

Next, the process may register (at 1770) the user, device, and cartridge. Such registration may include sending information from the dispensary device 1460 to the server 1420. The registration may include upload of user biographical information, user biometric data, device information (e.g., a unique identifier), cartridge information (e.g., a unique identifier), pharmacist or provider information, practitioner information, and/or other relevant information (e.g., device manufacturer, cartridge manufacturer, etc.). In some situations, registration may include associating entities to other already-existing system entities. For instance, an existing user may purchase an updated dosing device before refilling an existing prescription. In such a case, the user account and prescription may be associated with the new device and new cartridge when the patient performs the next refill.

Some embodiments may thus allow a comprehensive management system for use of controlled substances by linking the dosing device, cartridge housing the controlled substance, the patient, the physician, the pharmacy, the manufacturer, the central database of some embodiments, and centralized control (e.g., as facilitated by server 1420) such that there is virtually no way to abuse the system by providing controlled substances to unauthorized users.

In some embodiments, the user may perform a separate registration and/or a separate device registration. For instance, a user may access an application or web-based resource to create an account using the system of some embodiments. The user may be able to register a device, update user information, etc. through the application or web resource. A prescription and cartridge may then be associated with the already-registered user and device when the user visits a practitioner and/or supplier.

The process may then receive (at 1780) a confirmation code or other appropriate confirmation of authentication. The code may be received from the server 1420. Such a code may be retrieved from a database or lookup table. The code may be generated or retrieved based on information related to the user, dosing device, cartridge, prescription, practitioner, and/or supplier.

Process 1700 may then enable (at 1790) the dosing device and cartridge and then may end. Enabling the cartridge and device may require, for instance, entering the confirmation code at the terminal 1460, user device 1410, and/or dosing device 800 (e.g., via a wired or wireless connection). In addition, as described above, some embodiments may require a physical or digital key be available to unlock the device or cartridge in order to enable use. The terminal 1460 may generate and upload some enabling data to the device and/or cartridge based on the confirmation code or other authentication. Valid data may be recognized at the device and/or cartridge such that use is enabled.

Figure 18:
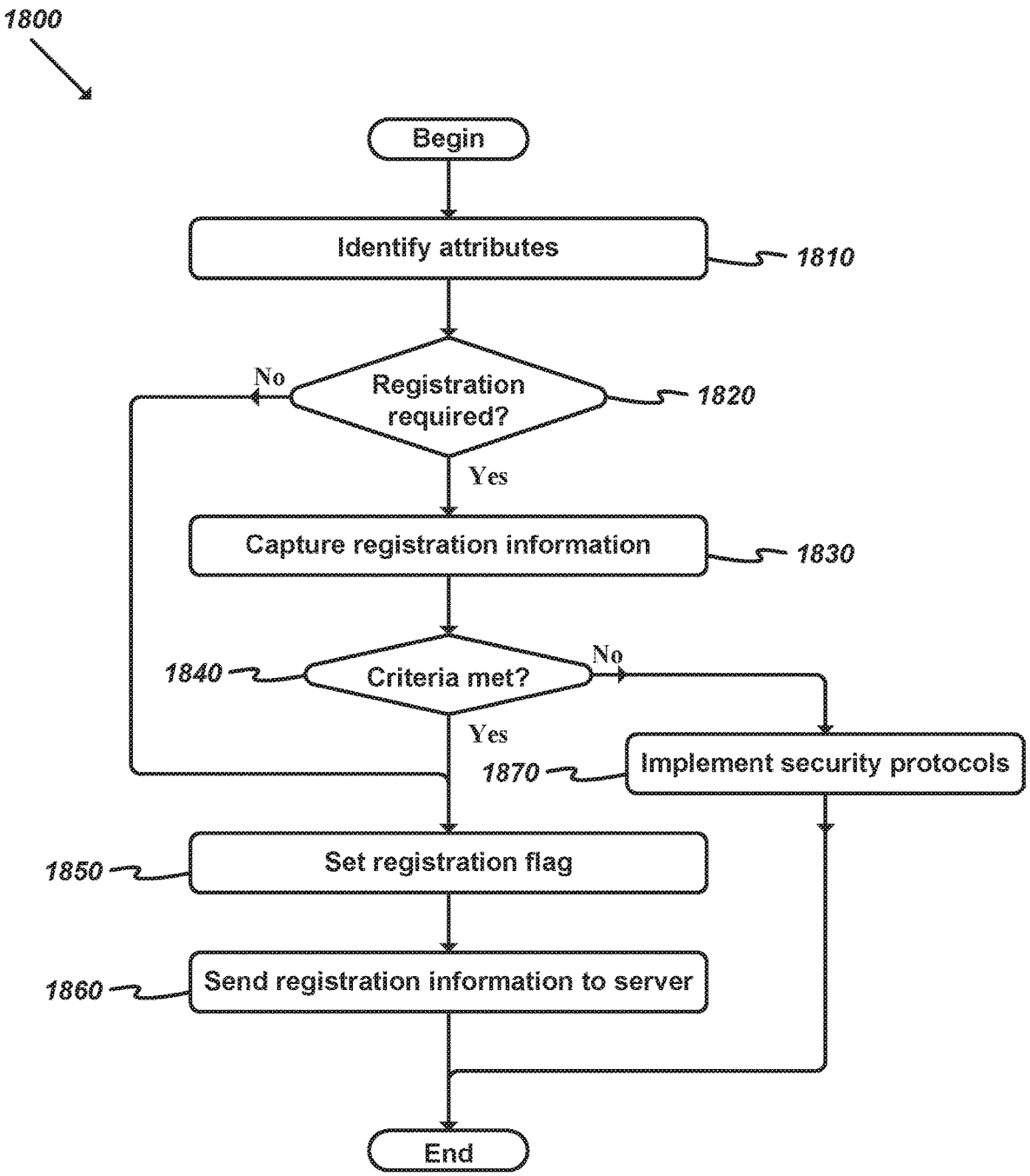
FIG. 18 illustrates a flow chart of an exemplary registration process performed by the dosing device of FIG. 8.

FIG. 18 illustrates a flow chart of an exemplary registration process 1800 performed by the dosing device 800. The user device 1410 and/or server 1420 may execute complementary processes. Process 1800 may utilize an application or other dedicated software running on device 800 and/or 1410. The process may enable use of a dosing device 800 by a user. In some embodiments, a user may be required to register a device before uploading a prescription, installing a cartridge, or otherwise utilize the device. As described above, the device registration process may be performed as part of a prescription fulfillment or generation process.

As shown, the process may identify (at 1810) device attributes. Such attributes may be retrieved by the device 800 itself or from a database associated with a resource such as server 1420. Device attributes may include a flag or other feature that indicates whether the device requires authentication, and/or whether the device has already been authenticated.

The process may determine (at 1820) whether registration is required. Some devices may support substances that do not require registration (e.g., a dosing device that generates saline mist). Users may still wish to monitor usage, dose amounts, etc. using the system of some embodiments. Other devices may require varying degrees of registration that may depend on the type and/or amounts of substances able to be provided by the dosing device.

If the process determines (at 1820) that registration is required, the process may capture (at 1830) the required registration information. Such information may include, for instance, biographic information (e.g., name, ID number, address, age, etc.), biometric data (e.g., fingerprint scan, facial scan, etc.), and/or other appropriate data (e.g., username and password). Such captured information may be stored as a reference for comparison to future data captures (e.g., subsequent fingerprint scans may be compared to a reference scan). In addition to, or in place of, user information, registration information may include, for instance, one or more activation or registration codes provided by a practitioner, pharmacist, and/or other appropriate resource. Such codes may be utilized to pair a user device 1410 to a dosing device 800, for instance.

Next, the process may determine (at 1840) whether the registration criteria have been met. Such a determination may be made in various appropriate ways. For instance, required registration information may be retrieved from a lookup table or database, or from the server 1420. The required information may be compared to the captured information to determine whether the required information has been provided, whether the formatting is valid, etc.

In addition, information may be pulled from related databases or other sources to verify user identity and/or data. For instance, users may be required to have an in-person verification at a practitioner or provider facility. As another example, a user may be required to have an existing patient ID with a particular provider, practitioner, facility, etc. before a device may be registered. User data (e.g., biographic data, treatment information, condition information, etc.) may be retrieved from a patient database based on the patient ID.

In some cases, a patient-user may not be able to appear in person to receive or fill a prescription. Likewise, some patient-users may not be capable of operating the dosing device 800 (e.g., due to age, physical or mental incapacity or impairment, etc.). In such cases, an authorized caregiver may be able to fulfill at least some registration requirements. The device 800 and/or cartridge 855 may be associated with the patient and/or the caregiver in such situations, as appropriate.

After determining (at 1840) that the registration criteria have been met, or after determining (at 1820) that registration is not required, the process may set (at 1850) a registration flag indicating that the device is ready for use.

The process may then send (at 1860) any collected registration information to the server 1420 and then may end. Such collected information may generally include at least a user identifier and a device identifier. In cases where registration is not required, no information may be sent to the server.

If the process determines (at 1870) that the registration criteria have not been met, the process may implement (at 1870) various security protocols and then may end. Such protocols may include, for instance, engaging (or failing to disengage) a physical lock associated with the device, disabling a connection port of the device (e.g., a cartridge connection port), etc. In some embodiments, a notification message or other indication may be provided to the user and the user may attempt to correct any defects or deficiencies in the captured data.

Figure 19:
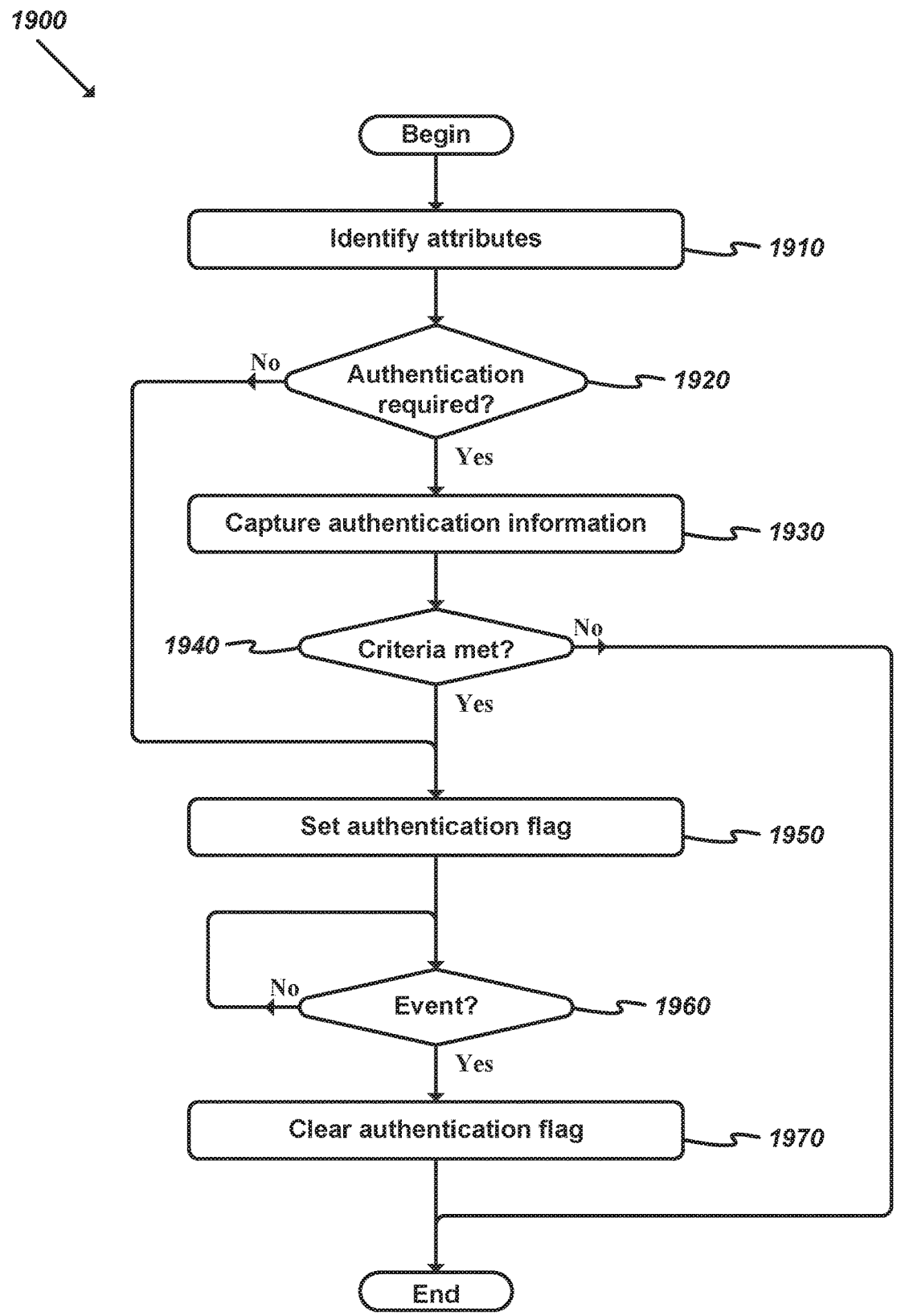
FIG. 19 illustrates a flow chart of an exemplary process that authenticates a device user.

FIG. 19 illustrates a flow chart of an exemplary process 1900 that authenticates a device user. Such a process may be executed by the dosing device 800 in some embodiments. The process may begin, for instance, when a UI element is activated (e.g., a button push is detected), when the device is powered on, etc.

As shown, the process may identify (at 1910) various usage attributes associated with the device 800, cartridge 855, user, etc. Such attributes may be retrieved and stored at the device 800 using a process such as a process 1500 described above.

Next, process 1900 may determine (at 1920) whether authentication is required. Such a determination may be made based on various relevant factors (e.g., cartridge type, substance type, whether the cartridge is associated with a prescription, user settings, etc.).

If the process determines (at 1920) that authentication is required, the process may capture (at 1930) authentication information. Such information may be captured using various appropriate resources (e.g., UI elements 815, sensors 820, a camera or scanner associated with user device 1410, etc.). Captured authentication information may include, for instance, fingerprint scans, photographs of facial features, personal identification number (PIN) or password, etc. Authentication information may be dependent on capabilities of the device 800 and/or whether the device is communicatively coupled to an external resource such as user device 1410 or server 1420. For instance, if the device 800 includes a single control button, the "password" may include a particular cadence of clicks (e.g., four clicks in a row).

Next, the process may determine (at 1940) whether the authentication criteria have been met. Such a determination may be made, for instance, based on matching between a current capture and previously captured data, facial recognition analysis, voice recognition analysis, etc.

Satisfaction of the authentication criteria may require a calculated matching value (e.g., a percentage match) to exceed a specified matching threshold. Similarly, facial recognition analysis, voice recognition analysis, and/or other types of analysis may generate a matching score or value that is able to be compared to a threshold score or value.

After determining (at 1940) that the criteria was met or determining (at 1920) that no authentication is required, the process may set (at 1950) an authentication flag indicating that use is permitted. Depending on the circumstances, such a flag may be set by default (e.g., for adult use of non-prescription substances).

Next, the process may determine (at 1960) whether a security event has occurred. Such events may be defined using various appropriate criteria. For instance, some embodiments may include an authentication timeout such that use has to be re-authenticated after some specified time period. As another example, some embodiments may require re-authorization for each dose to be dispensed. As still another example, some embodiments may require re-authorization if a link to a user device is broken (e.g., indicating that the dosing device 800 has exceeded a specified distance from the user device 1410). Some embodiments may monitor device position and/or movement using sensors 820 in order to determine whether a user has put down the device 800 or otherwise ceased use. Other types of events may include environmental events. For instance, some embodiments may include a thermometer and may indicate that a cartridge is no longer usable if it has been exposed to temperatures outside a specified range. As another example, such events may include comparison of current date and time to a specified expiration of the cartridge.

In some embodiments, a UI element, such as elements 620 or 720 may include scanning and/or analysis components such that as a dose is provided, fingerprint data is continually scanned and analyzed such that a user must maintain contact with the UI element throughout dosing in order to dispense a dose (or a full dose).

Some embodiments may utilize a continuous identification algorithm. If a continuous identification mode is enabled, the device 800 may require, for instance, continuous finger print detection during use, where such detection may be provided via a dedicated scanner or other appropriate interface element. Such a mode may prevent non-authorized use of the substance provided by the dosing device. Although a user may be able to circumvent such protection by holding the device for another person, such an approach requires knowledge of the authorized user, thus still providing a deterrent effect.

If the process determines (at 1960) that no event has been identified, the process may repeat operation 1960 (i.e., the authorization flag may remain set) until the process determines (at 1960) that an event has been identified. If the process determines (at 1960) that an event has been identified, the process may clear (at 1970) the authorization flag and then may end.

Process 1900 may be executed as a background process such that any security event identified at 1960 causes the authentication flag to be cleared, thus requiring authentication for further use.

Figure 20:
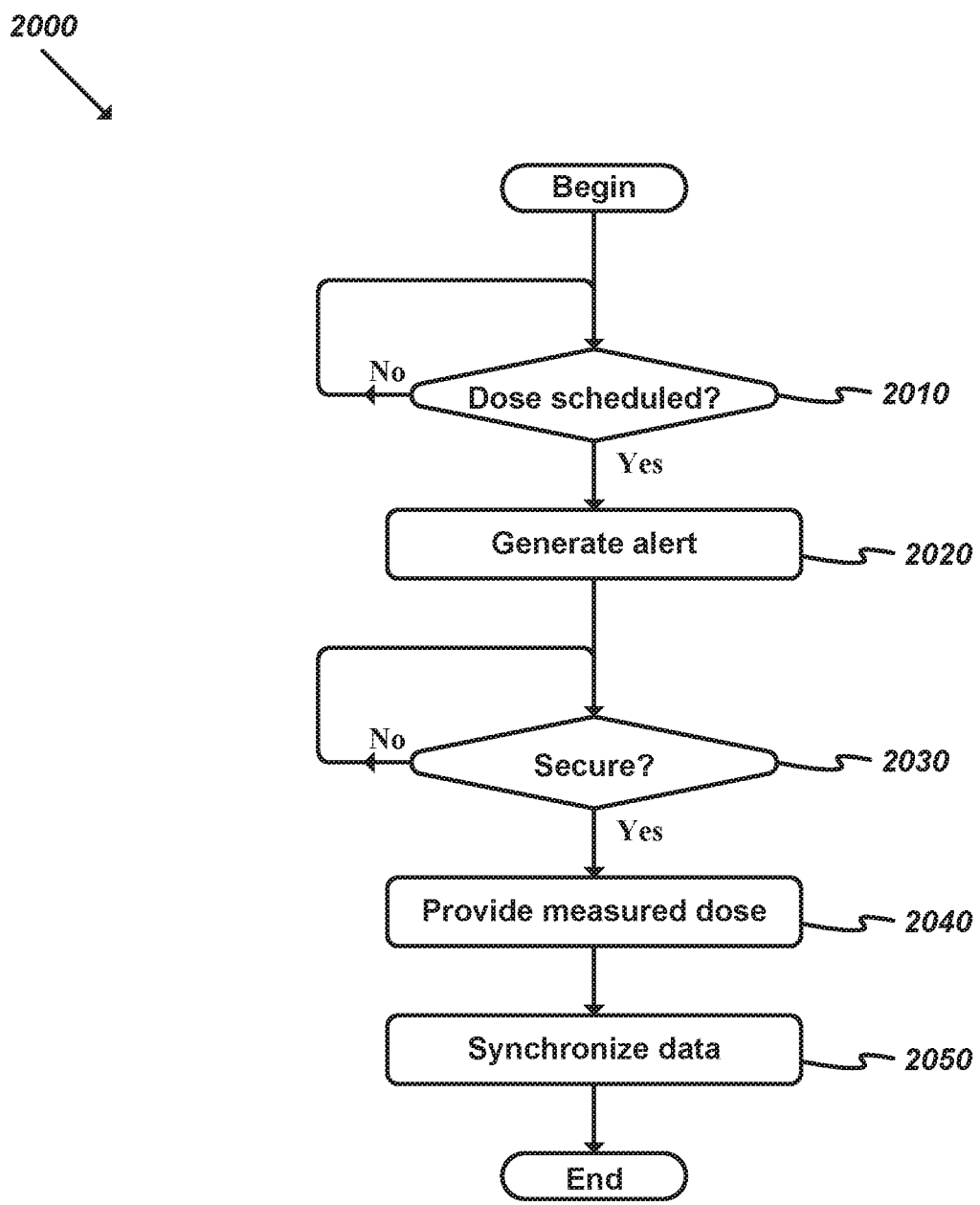
FIG. 20 illustrates a flow chart of an exemplary process that delivers a dose of a substance using the dosing device of FIG. 8.

FIG. 20 illustrates a flow chart of an exemplary process 2000 that delivers a dose of a substance using the dosing device 800. Such a process may be performed by a resource such as dispensary device 800. The user device 1410 and/or server 1420 may execute complementary processes. Process 2000 may utilize an application or other dedicated software running on device 800 or 1410.

As shown, the process may determine (at 2010) whether a dose is scheduled. The process may make such a determination in various appropriate ways (e.g., by comparing an elapsed time since a previous dose to a prescribed dose frequency, by comparing a current time to a next scheduled dose time, etc.).

If the process determines (at 2010) that no dose is scheduled, the process may repeat operation 2010 until the process determines (at 2010) that a dose is scheduled. If the process determines (at 2010) that a dose is scheduled, the process may generate (at 2020) an alert. Such an alert may be provided by the dosing device 800 and/or user device 1410. The alert may utilize UI elements 815 such as LED indicators, haptic elements (e.g., device vibration), speakers or audio outputs, etc. UI elements of the user device 1410 may also be utilized to generate alerts. Features such as alert generation may be configurable, such that a user may select whether to receive an alert, type of alert(s) to receive, timing of alert(s), etc.

Next, the process may determine (at 2030) whether the device is secure. Security may be authenticated in various appropriate ways, as described above in reference to process 1900 and the process may verify whether the authentication flag has been set. Some embodiments may utilize a built-in fingerprint scanner at the dosing device 800 to ensure that an authorized user is present during use.

If the process determines (at 2030) that the device is not secure or that use is not authorized, the process may repeat operation 2030 until the process determines (at 2030) that the device is secure. Some embodiments may include lockout or other such features that limit the number of allowed failed use attempts, failed attempts over a time period, etc.

If the process determines (at 2030) that the device is secure, the process may provide (at 2040) a measured dose. The dose may be provided using a process such as process 2100 described below.

Next, the process may synchronize (at 2050) data and then may end. Such synchronization may include sending information to the server 1420 such as dose time, dose amount, verification or authentication information (e.g., an image of a capture fingerprint), etc. The synchronization may further include downloading information from the server. Such synchronization may be applied to the user device 1410 as well as the dosing device 800.

Figure 21:
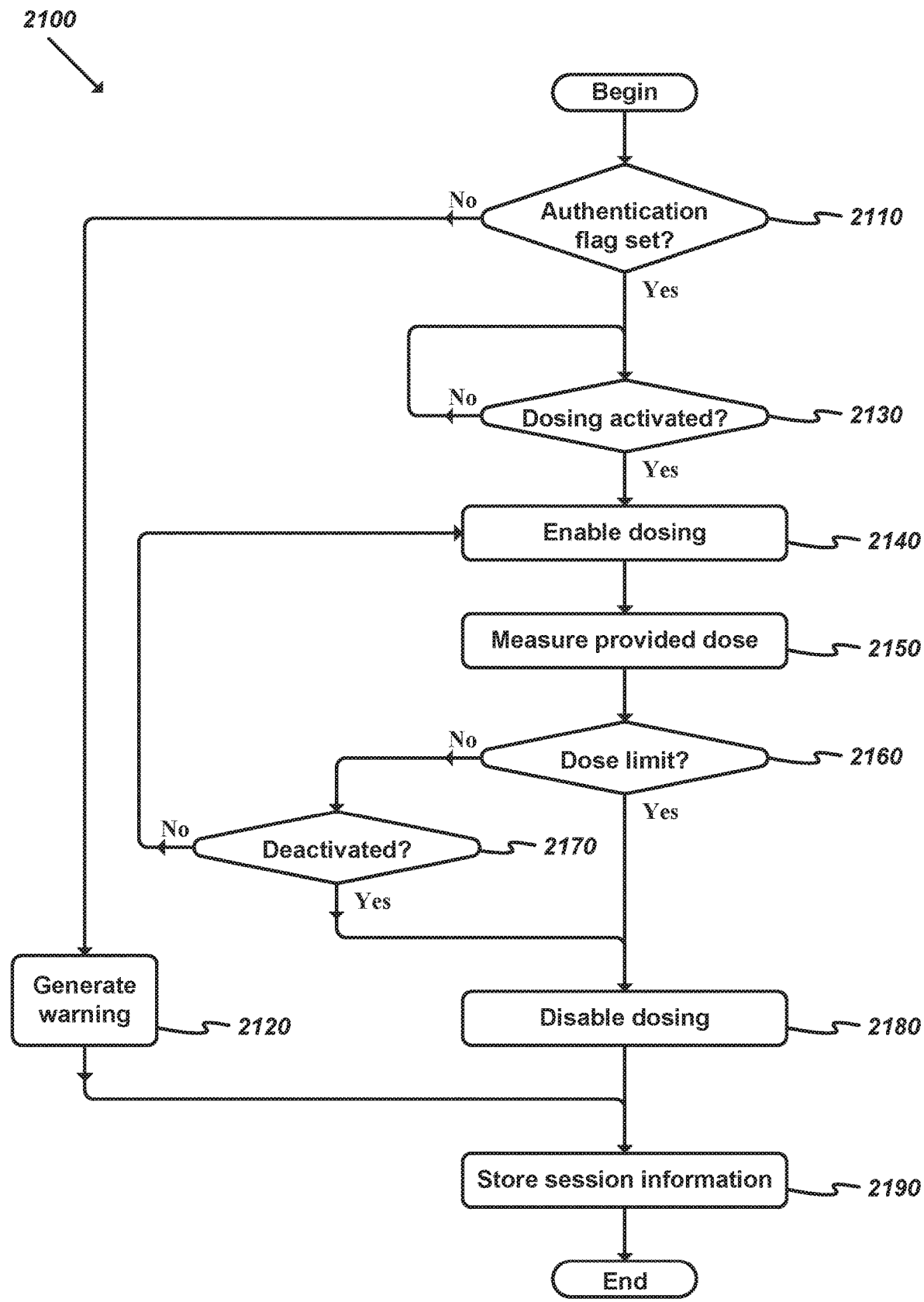
FIG. 21 illustrates a flow chart of an exemplary process that provides an inhaled substance using the dosing device of FIG. 8.

FIG. 21 illustrates a flow chart of an exemplary process 2100 that provides an inhaled substance using the dosing device 800. Similar processes may be implemented for different substance types. Such a process may be executed by the dosing device in some embodiments. The process may begin, for instance, when a UI element is activated (e.g., a button push is detected), when the device is powered on, etc.

As shown, the process may determine (at 2110) whether the authentication flag has been set. If the process determines (at 2110) that the flag has not been set, the process may generate (at 2120) a warning or error message. Such a message may be indicated at the device 800 (e.g., using a display, haptic feedback element, and/or other UI element 815) or via an external resource such as a user device 1410. The message may include an indication of actions required to authenticate use (e.g., scan fingerprint, capture facial photo, enter PIN or password, etc.).

If the process determines (at 2110) that the authentication flag has been set, the process may determine (at 2130) whether dosing has been activated. Such a determination may be made based on received inputs at the device 800 and/or other appropriate criteria. For instance, in some embodiments, a user may press and hold a button to dispense the substance. If the process determines (at 2130) that dosing has not been activated, the process may repeat operation 2130 until the process determines (at 2130) that dosing has been activated.

If the process determines (at 2130) that dosing has been activated, the process may enable (at 2140) dosing. Dosing may be enabled in various appropriate ways. One example is described in reference to process 2200 below. In some embodiments, dosing may be enabled by providing a substance in a discrete form (e.g., a single capsule or tablet). Some embodiments may process the substance in various ways (e.g., by atomizing or vaporizing the substance) using various components in order to provide the substance. Some embodiments may provide a measured amount for further processing before use (e.g., by providing an amount of a liquid or powdered substance for mixing with water).

Process 2100 may then measure (at 2150) the provided dose. Such measurement may be made by a resource such as flow meter 865. In some cases, a discrete dose may be provided rather than measured (e.g., a single capsule, a full scoop of a powdered substance to be mixed with water, etc.). In some such cases, pre-measured units or discrete doses may be provided rather than measured. For instance, a dose may be specified as a number of pills, where measurement involves releasing and providing the specified number of pills to the user.

Next, the process may determine (at 2160) whether there is a dose limit associated with the usage scenario. Such a dose limit may be associated with a cartridge, substance, prescription, user, etc. The dose limit may be associated with a single dispensed dose and/or usage over a period of time. If the process determines (at 2160) that there is no dose limit or that the dose limit has not been exceeded, the process may determine (at 2170) whether dosing has been deactivated. Such a determination may be made based on various relevant criteria (e.g., whether a button has been released, whether a temperature or other usage threshold has been exceeded, whether a maximum dose time has been exceeded, etc.).

If the process determines (at 2170) that dosing has not been deactivated, the process may repeat operations 2140-2170 until the process determines (at 2160) that the dose limit has been reached or determines (at 2170) that dosing has been deactivated. A dose limit may be a threshold value where the measured provided dose must meet or exceed the threshold value in order to constitute administration of a full dose.

If the process determines (at 2160) that the dose limit has been reached or determines (at 2170) that dosing has been deactivated, the process may disable (at 2180) dosing. Dosing may be disabled in various appropriate ways. One example is described in reference to process 2300 below.

After disabling (at 2180) dosing, or after generating (at 2120) the warning, the process may store (at 2190) session information and then may end. Such information may include, for instance, number of doses, total amount consumed, dose times and durations, authentication information, etc. The stored information may be provided to external resources such as user device 1410, server 1420, or storage 1430.

Figure 22:
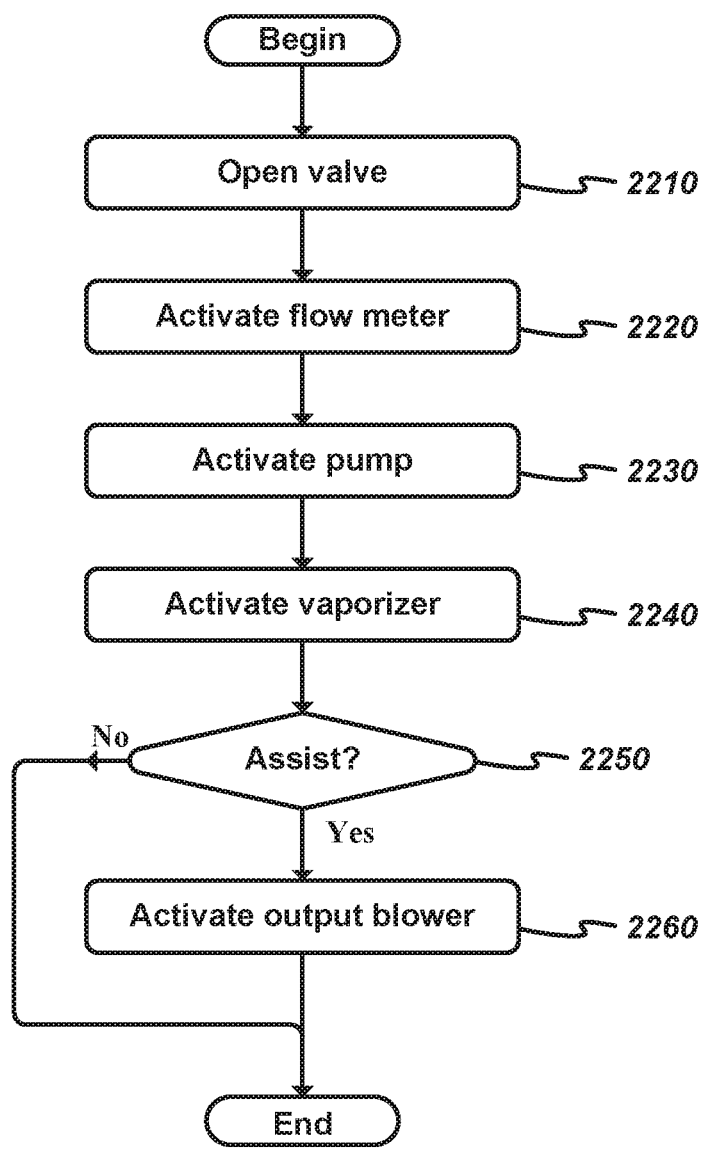
FIG. 22 illustrates a flow chart of an exemplary process that activates dosing using the dosing device of FIG. 8.

FIG. 22 illustrates a flow chart of an exemplary process 2200 that activates dosing using the dosing device 800. Such a process may be executed by the dosing device 800 in some embodiments. The process may be performed, for instance, as operation 2140 described above.

As shown, process 2200 may open (at 2210) a cartridge valve such as valve 860. Next, the process may activate (at 2220) a flow meter such as meter 865 (and/or other appropriate measurement resource such as a timer or counter).

Process 2200 may then activate (at 2230) a pump such as pump 870. Next, the process may activate (at 2240) a vaporizer or atomizer such as vaporizer 875. The process may then determine (at 2250) whether an assist should be provided by a resource such as output blower 880. Such a determination may be made based on various relevant criteria (e.g., substance attributes, cartridge attributes, user attributes and/or selections, etc.).

If the process determines (at 2250) that no assist is needed, the process may end. If the process determines (at 2250) that assist is needed, the process may activate (at 2260) the output blower 880 or other appropriate resource and then may end.

Figure 23:
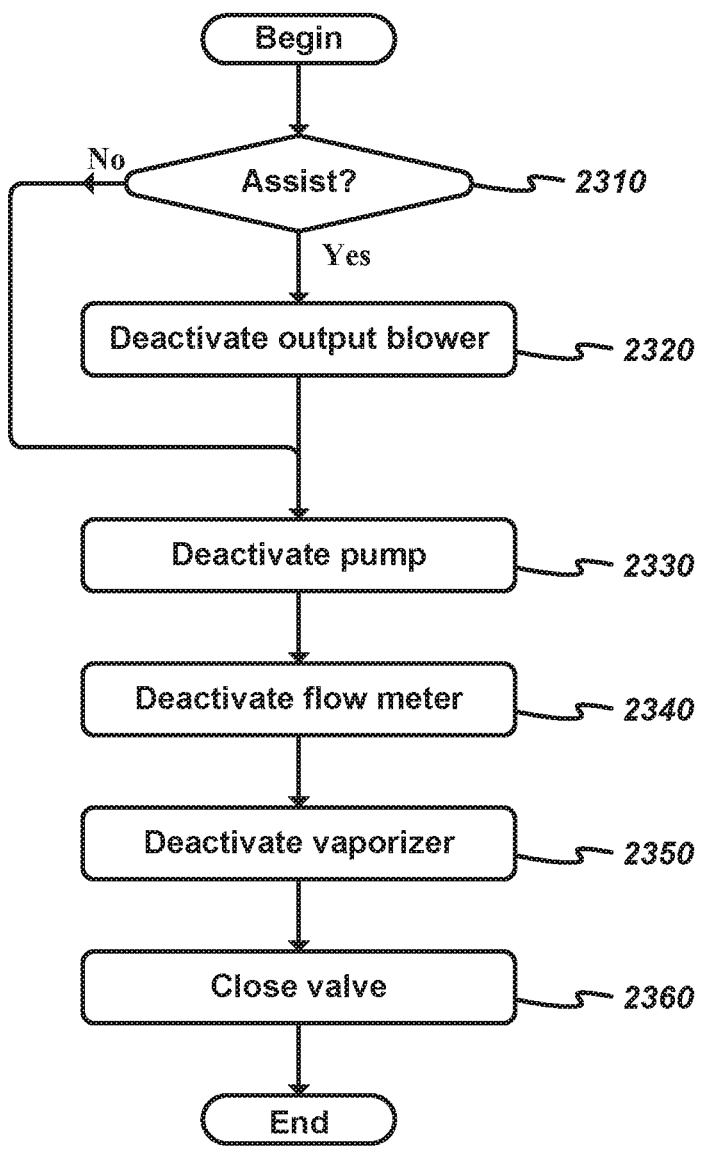
FIG. 23 illustrates a flow chart of an exemplary process that deactivates dosing using the dosing device of FIG. 8.

FIG. 23 illustrates a flow chart of an exemplary process 2300 that deactivates dosing using the dosing device 800. Such a process may be executed by the dosing device 800 in some embodiments. The process may be performed, for instance, as operation 2170 described above.

As shown, process 2300 may determine (at 2310) whether assist has been activated. Such a determination may be made in various appropriate ways (e.g., by polling a state of the output blower 880). If the process determines (at 2310) that assist is active, the process may deactivate (at 2320) the output blower 880 or other appropriate resource. After deactivating (at 2320) the output blower or after determining (at 2310) that assist was not active, the process may deactivate (at 2330) the pump 870 or other appropriate resource.

Next, the process may deactivate (at 2340) the flow meter 865 or other appropriate measurement resource. Process 2300 may then deactivate (at 2350) the vaporizer 875, close (at 2360) the valve 860, and then may end.

Different embodiments may deactivate the components in different orders depending on various relevant factors. For instance, a heating element associated with the vaporizer 875 or cartridge 855 may be deactivated before the output blower 880 is deactivated. As another example, the valve 860 may be closed before blower 880 is deactivated such that all vaporized substance is cleared from the flow pathway 890.

Processes 2200 and 2300 are generally applicable to inhaled substances. Similar processes may be implemented for other substance types depending on the substance attributes (e.g., form, dose, substance class, etc.) and depending on the elements of the delivery feature (e.g., feature 850, 1000, 1100, 1200, or 1300).

Figure 24:
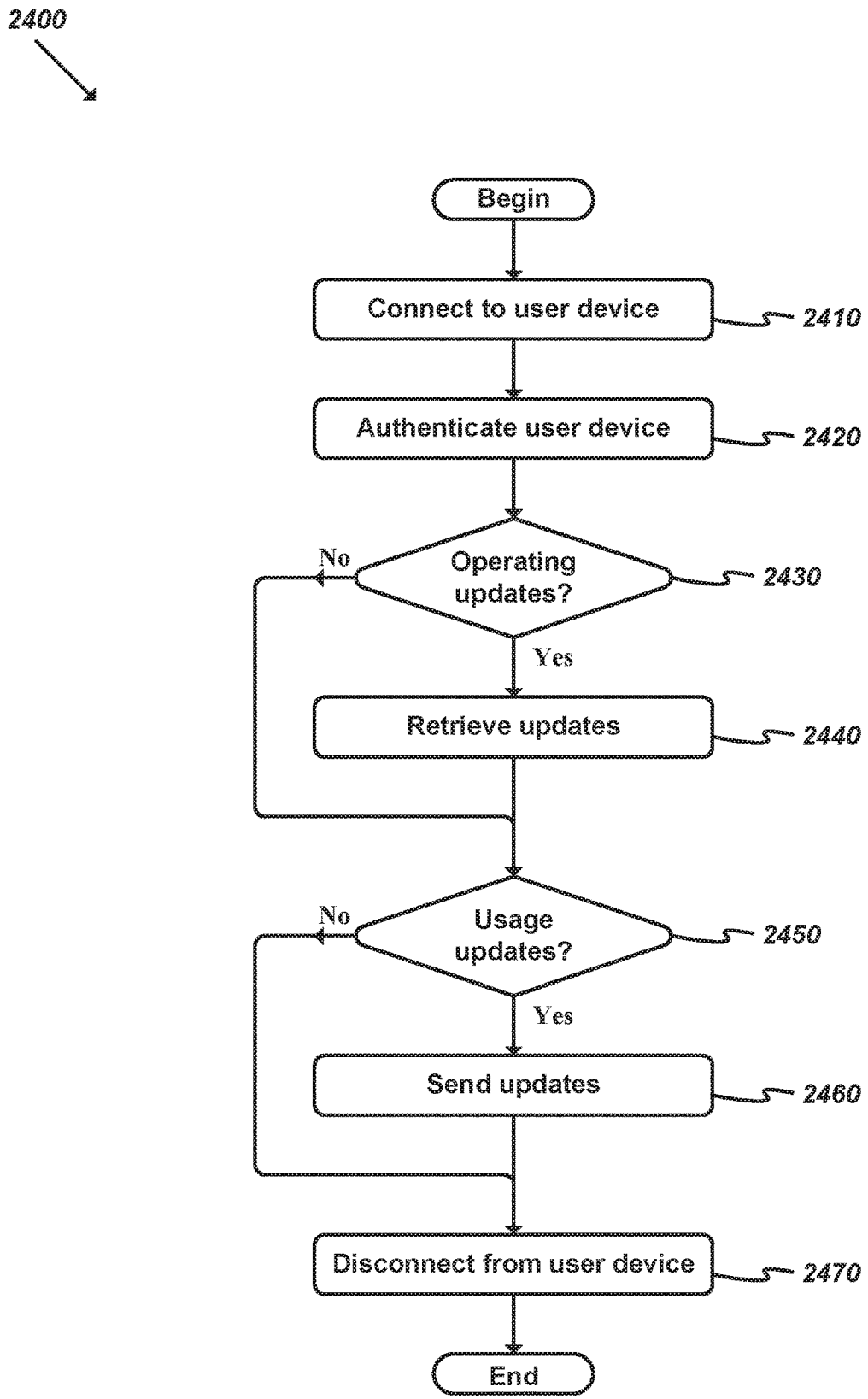
FIG. 24 illustrates a flow chart of an exemplary process that provides communication between the dosing device of FIG. 8 and a user device.

FIG. 24 illustrates a flow chart of an exemplary process 2400 that provides communication between the dosing device 800 and a user device. Such a process may be executed by the dosing device 800 in some embodiments. A complementary process may be executed by a device such as user device 1410. The process may begin, for instance, when the dosing device 800 is communicatively coupled to the user device 1410.

As shown, the process may connect (at 2410) the dosing device 800 to a user device such as device 1410. The connection may be via a wired or wireless communication channel. Next, the process may authenticate (at 2420) the user device. Such authentication may be based on various relevant criteria (e.g., entry of a PIN or password, facial or fingerprint scanning, verifying identifying information related to the device, etc.). For instance, in some embodiments, each user may have a list of associated dosing devices 800, user devices 1410, etc. Identifying information (e.g., MAC address, serial number, etc.) for authorized devices may be stored at the dosing device 800 and/or may be accessed via various external resources such as user device 1410, server 1420, or storage 1430.

If the device is unable to be authenticated (at 2420), a device authentication process may be executed. Such a process may collect the user device information, user information, password or PIN information, etc. and associate a user device 1410 to a dosing device 800. The device authentication process may require a physical connection between the dosing device 800 and user device 1410 (and/or other appropriate security measures, such as requiring a password or code included in the dosing device packaging). Such authentication or association may include registration via a server 1420 or other online resource. A user may be able to associate multiple user devices 1410 with a single dosing device 800 or multiple dosing devices with a single user device 1410.

In some scenarios, even non-authenticated user devices 1410 may be able to connect to an dosing device 800 without authentication. For example, a non-authenticated device 1410 may be able to connect and modify various settings (e.g., disable blower fan, adjust heat setting, etc.) but may not be able to access usage data or user information.

After authenticating (at 2420) a user device 1410, the process may determine (at 2430) whether there are any operating updates. Such a determination may be made in various appropriate ways. For instance, the dosing device may send a request to a server 1420 or storage 1430 for the latest version of software or other data available for use by the dosing device 800. Such a request may be sent via the user device 1410. The user device and/or dosing device 800 may likewise identify the version of software or data stored on the dosing device (and/or compare instantiations to identify any differences) and determine (at 2430) that there are operating updates when there is a difference between the instantiations or between the versions. Some embodiments may identify a time associated with the most recent update and determine (at 2430) that there are operating updates when a specified time period has passed since the most recent update.

If the process determines (at 2430) that there are operating updates, the process may retrieve (at 2440) the updates. Such updates may be retrieved from a resource such as server 1420 or storage 1430 and may be retrieved via the user device 1410. The updates may include software updates (e.g., firmware, interfaces, etc.) and/or parameter updates (e.g., operation settings, default values, etc.).

Such operating updates may also include user updates. For instance, after connecting the dosing device 800 to a user device 1410, a user device application of some embodiments may be launched. The user device application may include various UI elements that may allow a user to adjust settings, review usage history, etc. Such user updates may include initial device setup and registration, creation or association of user accounts, enabling or disabling of data sharing, etc.

After retrieving (at 2440) the updates or after determining (at 2430) that there are no operating updates, the process may determine (at 2450) whether there are usage updates. Such a determination may be made in various appropriate ways. For instance, a timestamp of the most recent usage session may be compared to a timestamp of the most recent uploaded session. As another example, the process may determine (at 2450) that there are usage updates if a specified time period has passed since the last updates (where such updates may also indicate no use during the specified time period).

If the process determines (at 2450) that there are usage updates, the process may send (at 2460) the updates to an external resource such as a user device 1410, server 1420, storage 1430, etc. Such updates may be sent via the user device 1410.

After sending (at 2460) the updates or after determining (at 2450) that there are no usage updates, the process may disconnect (at 2470) from the user device 1410 and then may end.

Figure 25:
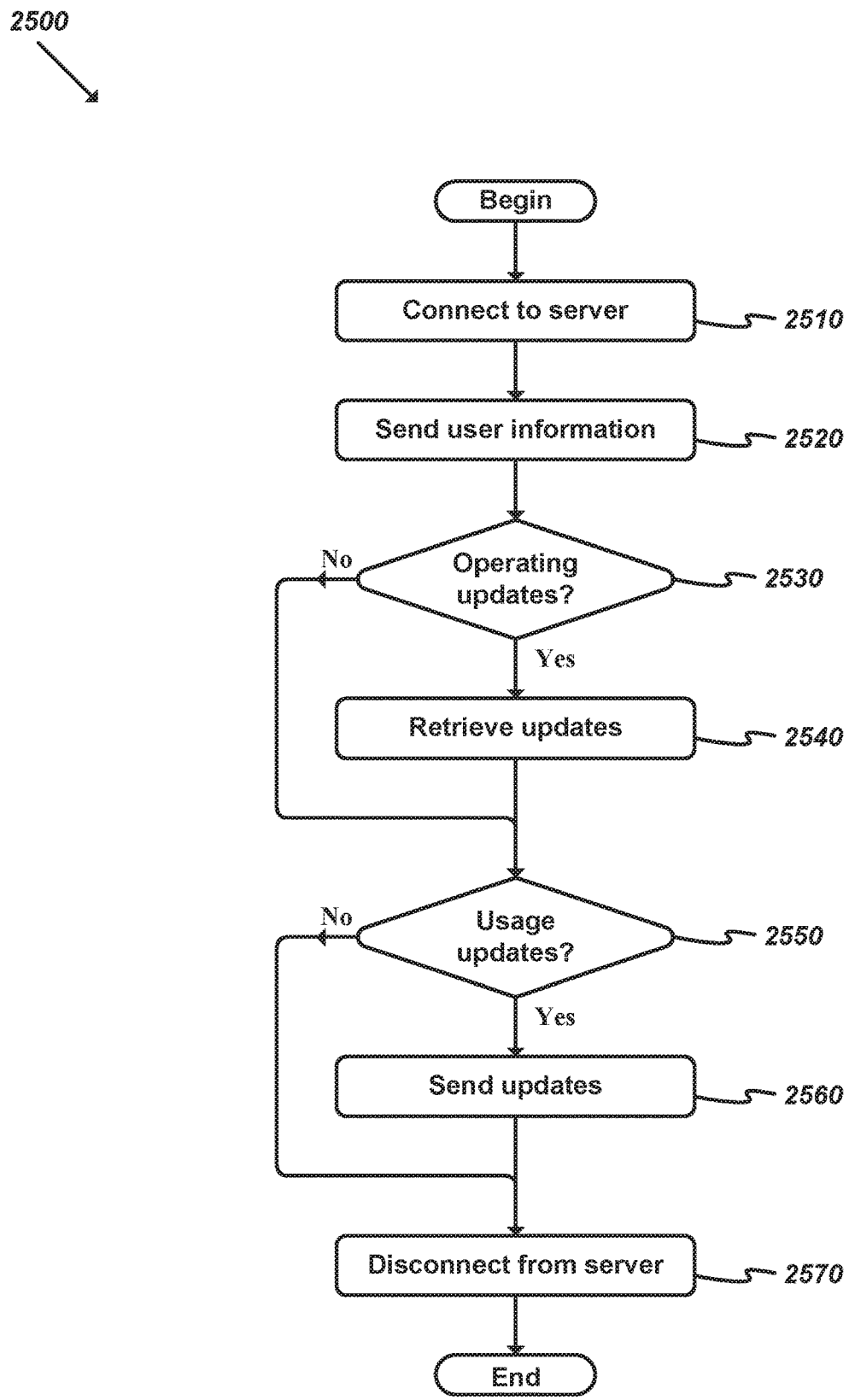
FIG. 25 illustrates a flow chart of an exemplary process that provides communication between a user device and a server of some embodiments.

FIG. 25 illustrates a flow chart of an exemplary process 2500 that provides communication between a user device and a server of some embodiments. Such a process may be executed by the user device 1410 in some embodiments.

Alternatively, the process may be executed by a dosing device 800 that is able to communicate with a server or other online resource. A complementary process may be executed by a device such as server 1420. The process may begin, for instance, when an application of some embodiments is launched, when the user device 1410 is communicatively coupled to the server 1420, etc.

In some cases, process 2500 may be executed by a practitioner device 1450 or dispensary device 1460 when connected to a dosing device 800 (e.g., when a patient does not have an appropriate user device, usage data may be downloaded when the patient return to the doctor's office or the pharmacy). In some situations, the device 800 may be owned by (or otherwise associated with) a practitioner, pharmacy, facility, etc. and may be provided to a patient for temporary use. In such cases, device data may be downloaded when the device is returned to the associated entity. For instance, a patient may receive a device from the pharmacy as part of a two-week prescription. The device and/or cartridge may include an amount of the substance matching the full prescription. Once the patient has completed the prescribed regimen, the patient may return the device to the provider, where data may be retrieved, and the device may be refilled, cleaned, initialized, and/or otherwise readied for another user.

As shown, the process may connect (at 2510) to a server such as server 1420. Alternatively, the process may connect to a resource such as storage 1430 via an API or other appropriate interface. In addition, the dosing device 800 and/or user device 1410 may execute applications of some embodiments.

Next, the process may send (at 2520) user information. Such information may include, for instance, identifying information such as a username, authenticating information such as a password, and/or other appropriate user information. In addition, such information may include, for instance, dosing device identifying information (e.g., serial number), user device identifying information (e.g., MAC address, serial number, etc.), current versions of software or operating parameters, timestamp of last updates, timestamp of last dosing device 0100 use, etc.

The user device 1410 may be authenticated in various appropriate ways (e.g., by comparing identifying information such as MAC address to a list of authorized devices associated with a user account). If the user device has not previously been authorized, an error or warning message may be sent and the process may end.

In addition to sending (at 2520) user information, the process may retrieve information from the server or other resource. Such information may include, for instance, a latest version of software and/or operating parameters, timestamp of last connection, etc.

After sending (at 2520) user information and/or retrieving server information, the process may determine (at 2530) whether there are any operating updates. Such a determination may be made in various appropriate ways. For instance, the versions of installed software may be compared to versions of available software. Some embodiments may identify a time associated with the most recent update and determine (at 2530) that there are operating updates when a specified time period has passed since the most recent update.

If the process determines (at 2530) that there are operating updates, the process may retrieve (at 2540) the updates. Such updates may be retrieved from a resource such as server 1420 or storage 1430 and may be retrieved via the user device 1410. The updates may include software updates (e.g., firmware, interfaces, etc.) and/or parameter updates (e.g., operation settings, default values, etc.). Such updates may include updates to the applications executed by the dosing device 800 and/or user device 1410 in some embodiments. In addition to updates, initial installations may be performed in a similar manner.

Such operating updates may also include user updates. For instance, after connecting the dosing device 800 to a user device 1410, a user device application of some embodiments may be launched. The user device application may include various UI elements that may allow a user to adjust settings, review usage history, etc. Such user updates may include initial device setup and registration, creation or association of user accounts, enabling or disabling of data sharing, etc.

After retrieving (at 2540) the updates or after determining (at 2530) that there are no operating updates, the process may determine (at 2550) whether there are usage updates. Such a determination may be made in various appropriate ways. For instance, a timestamp of the most recent usage session may be compared to a timestamp of the most recent uploaded session. As another example, the process may determine (at 2550) that there are usage updates if a specified time period has passed since the last updates (where such updates may also indicate no use during the specified time period). In some embodiments, usage information may be uploaded from the dosing device 800 to a device such as user device 1410 using a process such as process 2400. The usage information may be stored at the user device until a process such as process 2500 is executed.

If the process determines (at 2550) that there are usage updates, the process may send (at 2560) the updates to an external resource such as server 1420, storage 1430, etc.

After sending (at 2560) the updates or after determining (at 2550) that there are no usage updates, the process may disconnect (at 2570) from the server 1420 and then may end.

Figure 26:
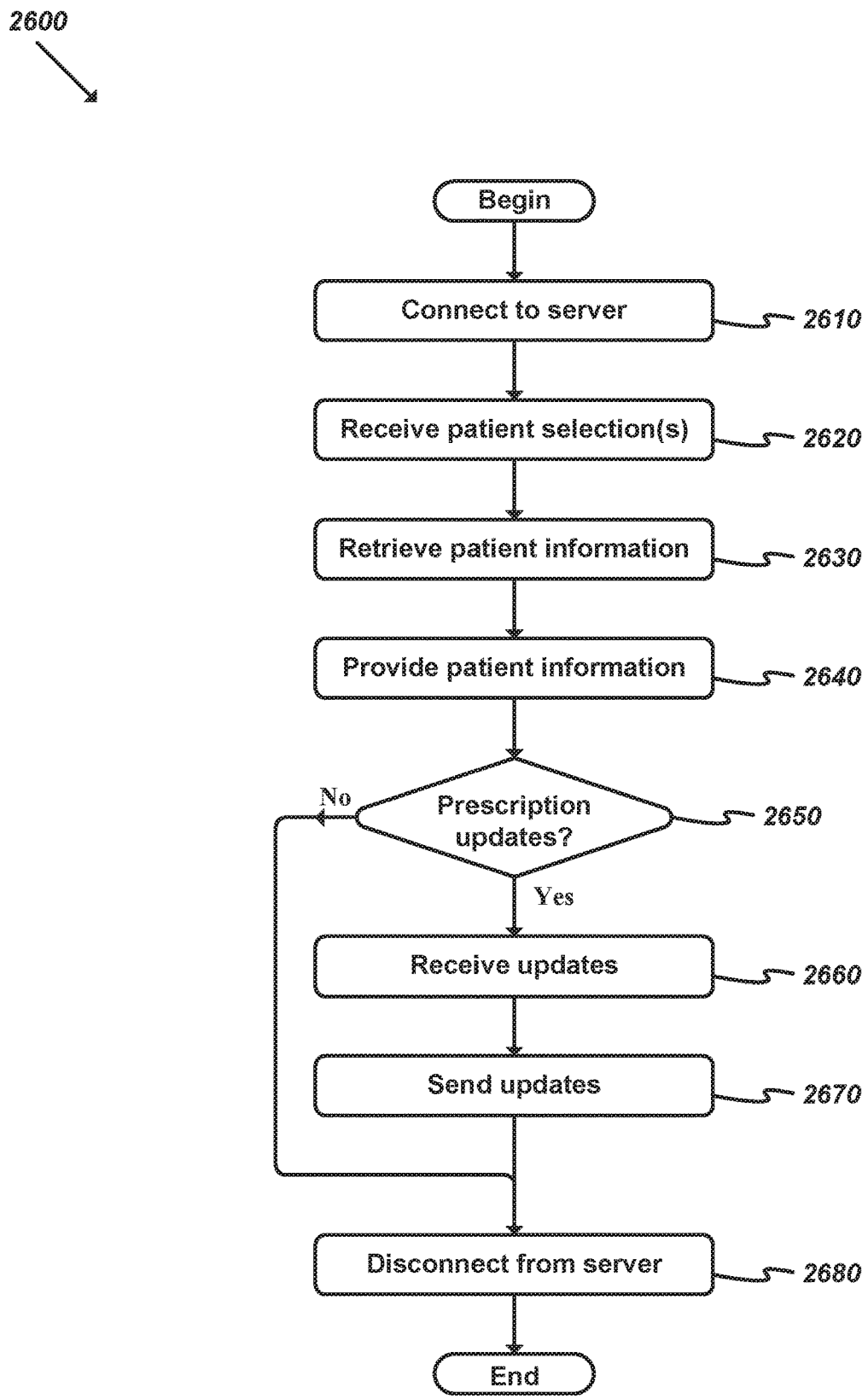
FIG. 26 illustrates a flow chart of an exemplary process that provides communication between a practitioner device and a server of some embodiments.

FIG. 26 illustrates a flow chart of an exemplary process 2600 that provides communication between a practitioner device 1450 and a server 1420. Such a process may be performed by a resource such as practitioner device 1450. A similar process may be executed by a dispensary device 1460. The server 1420 may execute a complementary process. Process 2600 may utilize an application or other dedicated software running on device 1450. The process may allow a physician or supplier to monitor patient use, update prescription or usage information, and/or otherwise interact with the system of some embodiments.

As shown, process 2600 may connect (at 2610) to a server such as server 1420. Alternatively, the process may connect to a resource such as storage 1430 via an API or other appropriate interface.

Next, the process may receive (at 2620) one or more patient selections. Such selections may be made in various appropriate ways. For instance, a list of patients associated with the practitioner may be provided, from which any number of patient selections may be made. Alternatively, a patient ID or identifying information (e.g., last name) may be used to identify the desired selections. In some embodiments, the list of patients may be limited to patients for whom the practitioner has written a prescription. The list of patients may be otherwise limited, as appropriate (e.g., practitioners associated with a group or facility may be able to access data related to all patients associated with the group or facility).

The process may then retrieve (at 2630) patient information related to the selected patients. Such information may include, for instance, usage information including dose and schedule, prescription activity (e.g., whether filled, times refilled, etc.), patient feedback, test results or in-home measurements, etc.

Process 2600 may then display or otherwise provide (at 2640) the retrieved information to the practitioner. The information may be provided using various appropriate graphical user interfaces or other appropriate features that may be optimized for a particular device type or otherwise customized based on various relevant factors (e.g., user preferences, type of data, number of patients, etc.). The data may be able to be filtered in various ways (e.g., by limiting to a certain date range, limiting to particular patients, etc.).

Next, the process may determine (at 2650) whether there are prescription updates. Such a determination may be made based on various relevant factors such as practitioner selection, change in user history or status, etc. If the process determines (at 2650) that there are prescription updates, the process may receive (at 2660) the updates. Such updates may be generated by the practitioner or may be automatically generated based on patient status, test data, etc. For instance, a refill order may be automatically generated if a patient meets some evaluation criteria. In this way, a practitioner may be able to actively monitor and control dose amounts, delivery schedules, reminders and notices, etc.

The process may then send (at 2670) the received updates to the server 1420 for dissemination to the appropriate dosing devices 800 and/or user devices 1410. Next, process 2600 may disconnect (at 2680) from the server and then may end.

One of ordinary skill in the art will recognize that, for brevity and clarity, various authentication operations and/or requirements may have been omitted from the above description. For instance, each practitioner device 1450 may implement security features such as login credentials, two-part authentication, key cards, access restrictions, etc. to safeguard the device and use thereof. Such protocols may be implemented by other parties, such as a pharmacy, a user, a device provider, etc.

One of ordinary skill in the art will recognize that processes 1500-2600 may be performed in various different ways without departing from the scope of the disclosure. For instance, the listed operations may be performed in different orders than shown. In addition, some embodiments may include additional operations and/or omit one or more listed operations. Operations and/or sets of operations may be performed iteratively and/or based on various performance criteria. Each process may be divided into multiple sub-processes and/or included as part of a larger macro process.

IV. Exemplary System and Device(s)

The processes and modules described above may be at least partially implemented as software processes that may be specified as one or more sets of instructions recorded on a non-transitory storage medium. These instructions may be executed by one or more computational element(s) (e.g., microprocessors, microcontrollers, digital signal processors (DSPs), application-specific integrated circuits (ASICs), field programmable gate arrays (FPGAs), other processors, etc.) that may be included in various appropriate devices in order to perform actions specified by the instructions.

As used herein, the terms "computer-readable medium" and "non-transitory storage medium" are entirely restricted to tangible, physical objects that store information in a form that is readable by electronic devices.

Figure 27:
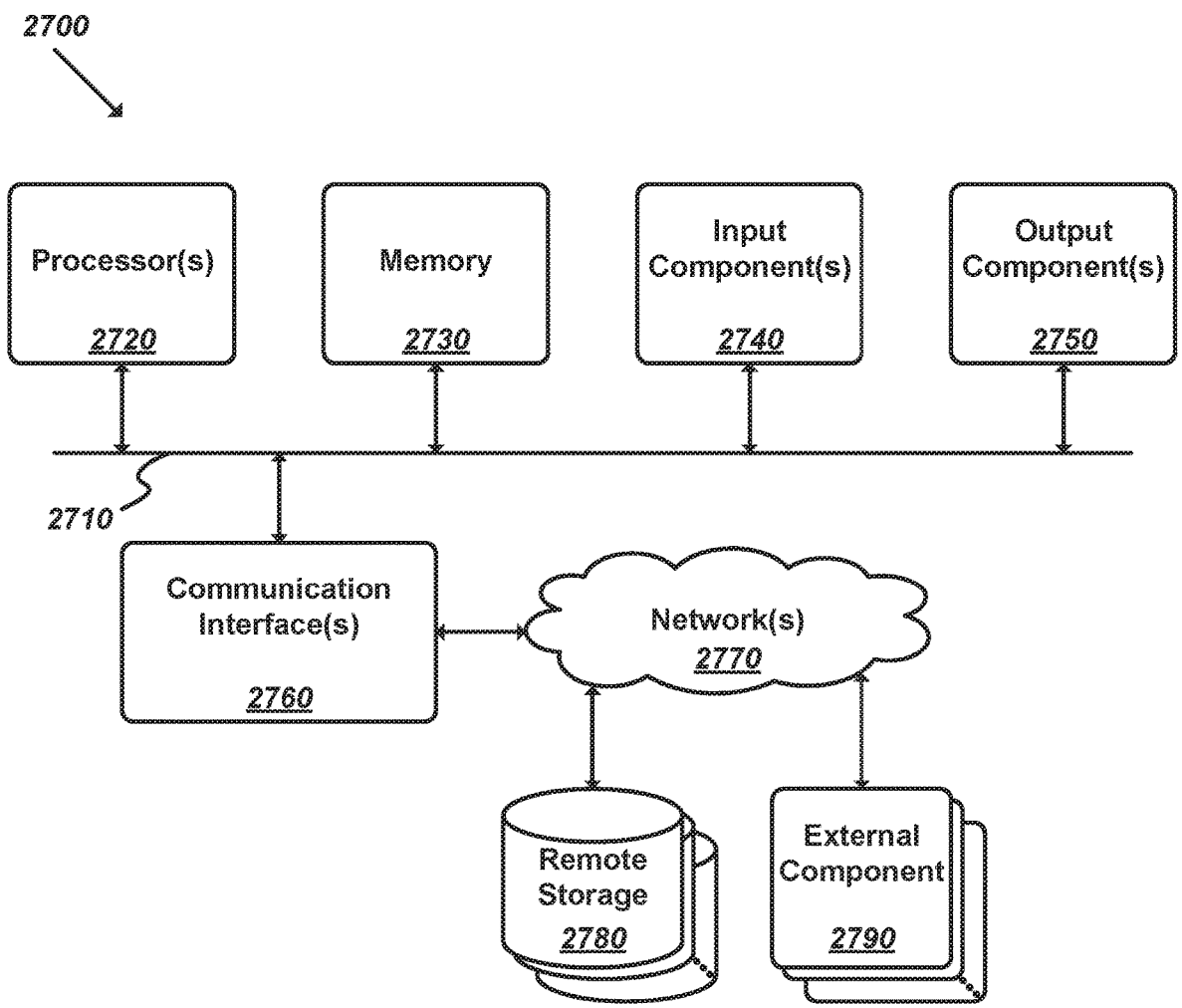
FIG. 27 illustrates a schematic block diagram of an exemplary computer system used to implement some embodiments.

FIG. 27 illustrates a schematic block diagram of an exemplary device (or system or devices) 2700 used to implement some embodiments. For example, the system described above in reference to FIG. 14 may be at least partially implemented using device 2700. As another example, the devices described above in reference to FIG. 6, FIG. 7, and FIG. 8 may be at least partially implemented using device 2700. As still another example, the processes described in reference to FIG. 15-FIG. 26 may be at least partially implemented using device 2700.

Device 2700 may be implemented using various appropriate elements and/or sub-devices. For instance, device 2700 may be implemented using one or more personal computers (PCs), servers, mobile devices (e.g., smartphones), tablet devices, wearable devices, and/or any other appropriate devices. The various devices may work alone (e.g., device 2700 may be implemented as a single smartphone) or in conjunction (e.g., some components of the device 2700 may be provided by a mobile device while other components are provided by a server).

As shown, device 2700 may include at least one communication bus 2710, one or more processors 2720, memory 2730, input components 2740, output components 2750, and one or more communication interfaces 2760.

Bus 2710 may include various communication pathways that allow communication among the components of device 2700. Processor 2720 may include a processor, microprocessor, microcontroller, digital signal processor, logic circuitry, and/or other appropriate processing components that may be able to interpret and execute instructions and/or otherwise manipulate data. Memory 2730 may include dynamic and/or non-volatile memory structures and/or devices that may store data and/or instructions for use by other components of device 2700. Such a memory device 2730 may include space within a single physical memory device or spread across multiple physical memory devices.

Input components 2740 may include elements that allow a user to communicate information to the computer system and/or manipulate various operations of the system. The input components may include keyboards, cursor control devices, audio input devices and/or video input devices, touchscreens, motion sensors, etc. Output components 2750 may include displays, touchscreens, audio elements such as speakers, indicators such as light-emitting diodes (LEDs), printers, haptic or other sensory elements, etc. Some or all of the input and/or output components may be wirelessly or optically connected to the device 2700.

Device 2700 may include one or more communication interfaces 2760 that are able to connect to one or more networks 2770 or other communication pathways. For example, device 2700 may be coupled to a web server on the Internet such that a web browser executing on device 2700 may interact with the web server as a user interacts with an interface that operates in the web browser. Device 2700 may be able to access one or more remote storages 2780 and one or more external components 2790 through the communication interface 2760 and network 2770. The communication interface(s) 2760 may include one or more application programming interfaces (APIs) that may allow the device 2700 to access remote systems and/or storages and also may allow remote systems and/or storages to access device 2700 (or elements thereof).

It should be recognized by one of ordinary skill in the art that any or all of the components of computer system 2700 may be used in conjunction with some embodiments. Moreover, one of ordinary skill in the art will appreciate that many other system configurations may also be used in conjunction with some embodiments or components of some embodiments.

In addition, while the examples shown may illustrate many individual modules as separate elements, one of ordinary skill in the art would recognize that these modules may be combined into a single functional block or element. One of ordinary skill in the art would also recognize that a single module may be divided into multiple modules.

Device 2700 may perform various operations in response to processor 2720 executing software instructions stored in a computer-readable medium, such as memory 2730. Such operations may include manipulations of the output components 2750 (e.g., display of information, haptic feedback, audio outputs, etc.), communication interface 2760 (e.g., establishing a communication channel with another device or component, sending and/or receiving sets of messages, etc.), and/or other components of device 2700.

The software instructions may be read into memory 2730 from another computer-readable medium or from another device. The software instructions stored in memory 2730 may cause processor 2720 to perform processes described herein. Alternatively, hardwired circuitry and/or dedicated components (e.g., logic circuitry, ASICs, FPGAs, etc.) may be used in place of or in combination with software instructions to implement processes described herein. Thus, implementations described herein are not limited to any specific combination of hardware circuitry and software.

The actual software code or specialized control hardware used to implement an embodiment is not limiting of the embodiment. Thus, the operation and behavior of the embodiment has been described without reference to the specific software code, it being understood that software and control hardware may be implemented based on the description herein.

While certain connections or devices are shown, in practice additional, fewer, or different connections or devices may be used. Furthermore, while various devices and networks are shown separately, in practice the functionality of multiple devices may be provided by a single device or the functionality of one device may be provided by multiple devices. In addition, multiple instantiations of the illustrated networks may be included in a single network, or a particular network may include multiple networks. While some devices are shown as communicating with a network, some such devices may be incorporated, in whole or in part, as a part of the network.

Some implementations are described herein in conjunction with thresholds. To the extent that the term "greater than" (or similar terms) is used herein to describe a relationship of a value to a threshold, it is to be understood that the term "greater than or equal to" (or similar terms) could be similarly contemplated, even if not explicitly stated. Similarly, to the extent that the term "less than" (or similar terms) is used herein to describe a relationship of a value to a threshold, it is to be understood that the term "less than or equal to" (or similar terms) could be similarly contemplated, even if not explicitly stated. Further, the term "satisfying," when used in relation to a threshold, may refer to "being greater than a threshold," "being greater than or equal to a threshold," "being less than a threshold," "being less than or equal to a threshold," or other similar terms, depending on the appropriate context.

No element, act, or instruction used in the present application should be construed as critical or essential unless explicitly described as such. An instance of the use of the term "and," as used herein, does not necessarily preclude the interpretation that the phrase "and/or" was intended in that instance. Similarly, an instance of the use of the term "or," as used herein, does not necessarily preclude the interpretation that the phrase "and/or" was intended in that instance. Also, as used herein, the article "a" is intended to include one or more items and may be used interchangeably with the phrase "one or more." Where only one item is intended, the terms "one," "single," "only," or similar language is used. Further, the phrase "based on" is intended to mean "based, at least in part, on" unless explicitly stated otherwise.

The foregoing relates to illustrative details of exemplary embodiments and modifications may be made without departing from the scope of the disclosure. Even though particular combinations of features are recited in the claims and/or disclosed in the specification, these combinations are not intended to limit the possible implementations of the disclosure. In fact, many of these features may be combined in ways not specifically recited in the claims and/or disclosed in the specification. For instance, although each dependent claim listed below may directly depend on only one other claim, the disclosure of the possible implementations includes each dependent claim in combination with every other claim in the claim set.

We claim:

1. A smart dosing device comprising:
   a supply pathway comprising a cartridge receptacle that is able to house a cartridge;
   a first sensor that captures identifying information related to the cartridge, and a second sensor;
   a wireless communication module, wherein a prescription is received by the smart dosing device;
   and at least one security feature that restricts use of the smart dosing device, wherein:
      the smart dosing device is associated with a unique device identifier (ID) comprising a first serial number,
      the cartridge is associated with a unique cartridge ID comprising a second serial number, wherein the unique cartridge ID is retrieved by the first sensor, wherein:
         the cartridge comprises a substance associated with the prescription,
         the prescription comprises a specified dose amount, specified dose frequency, and specified maximum dose over time, and
         the prescription is associated with prescription information stored at the smart dosing device, the prescription information comprising the unique device ID, a unique prescription cartridge ID, and user reference data, the user reference data comprising a fingerprint scan or facial photograph associated with a user, and
      use of the smart dosing device is disabled unless user data captured by the second sensor matches the user reference data and the unique cartridge ID matches the unique prescription cartridge ID.

2. The smart dosing device of claim 1, wherein the supply pathway further comprises a measurement element that detects an amount of a substance provided by the smart dosing device.

3. The smart dosing device of claim 2 further comprising a storage that collects usage information related to the smart dosing device.

4. The smart dosing device of claim 3, wherein the usage information comprises a quantity measured by the measurement element, identifying information related to the cartridge including the unique cartridge ID, a number of doses administered, and a timestamp associated with each administered dose.

5. The smart dosing device of claim 1, wherein the first sensor comprises a camera and the identifying information comprises a graphic code.

6. The smart dosing device of claim 1, wherein the first sensor comprises a near field communication (NFC) receiver and the identifying information comprises an NFC tag.

7. The smart dosing device of claim 1, wherein a metered dose is provided based on an amount determined by a measurement element located along the supply pathway.

8. The smart dosing device of claim 1, wherein the cartridge comprises a storage cavity that houses a substance comprising at least one of an opioid, cannabinoid, and nicotine-based substance.

9. The smart dosing device of claim 1, wherein the wireless communication module communicatively couples the smart dosing device to an external device, the external device comprising at least one of a smartphone, tablet, personal computer, server, and storage.

10. A method of providing a measured dose using a smart dosing Device comprising a first sensor, a second sensor, a third sensor and a wireless communication module, the method comprising:
retrieving, by the smart dosing device, a prescription specifying a substance, dose threshold, and dosing schedule;
associating the prescription to the smart dosing device, a cartridge housing the substance, and a user of the smart dosing device, wherein the cartridge is associated with a prescription cartridge serial number and the user is associated with biometric reference data, wherein the prescription cartridge serial number and the biometric reference data is stored at the smart dosing device;
capturing, at the smart dosing device, biometric data associated with the user by the first sensor and capturing, at the smart dosing device, a cartridge serial number by the second sensor;
disabling dosing when the captured serial number does not match the cartridge serial number or the biometric data does not match the biometric reference data;
enabling dosing when the captured serial number matches the prescription cartridge serial number and the captured biometric data matches the biometric reference data;
measuring a provided dose by the third sensor; and
disabling dosing when the provided dose exceeds the dose threshold.

11. The method of claim 10, wherein enabling dosing comprises:
activating an atomizer; and
activating a flow meter.

12. The method of claim 10, wherein enabling dosing comprises:
opening a latch;
extracting a measured portion of a substance; and
providing the measured portion through an outlet port.

13. The method of claim 10, wherein enabling dosing comprises:
activating an actuator; and
providing at least one of a tablet, capsule, or pill through an outlet port.

14. The method of claim 10, wherein the captured biometric data comprises at least one of a fingerprint scan and a facial photograph.

15. The method of claim 10, wherein the smart dosing device dispenses a substance comprising at least one of an opioid, cannabinoid, and nicotine-based solution.

* * * * *